United States Patent [19]
Murphy-Chutorian et al.

[11] Patent Number: 5,999,678
[45] Date of Patent: *Dec. 7, 1999

[54] LASER DELIVERY MEANS ADAPTED FOR DRUG DELIVERY

[75] Inventors: Douglas Murphy-Chutorian; Richard L. Mueller; Stuart D. Harman; Steve A. Daniel, all of Sunnyvale; Larry Witham, Palo Alto; Bruce Richardson, San Jose, all of Calif.

[73] Assignee: Eclipse Surgical Technologies, Inc., Sunnyvale, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/773,430

[22] Filed: Dec. 27, 1996

[51] Int. Cl.$^6$ .............................. G02B 6/06; A61B 17/36; A61M 31/00
[52] U.S. Cl. .............................. 385/117; 606/15; 606/16; 604/21; 604/49; 604/51; 604/53
[58] Field of Search .......................... 385/117–118, 115; 606/15–16, 7, 13, 20, 21, 30, 31, 49, 53, 22, 65–67; 604/49, 50, 51, 52, 53

[56] References Cited

U.S. PATENT DOCUMENTS

| | | | |
|---|---|---|---|
| 4,658,817 | 4/1987 | Hardy | 128/303.1 |
| 4,997,431 | 3/1991 | Isner et al. | 606/15 |
| 5,246,437 | 9/1993 | Abela | 606/5 |
| 5,380,316 | 1/1995 | Aita et al. | 606/7 |
| 5,386,837 | 2/1995 | Sterzer | 128/898 |
| 5,389,096 | 2/1995 | Aita et al. | 606/15 |
| 5,498,238 | 3/1996 | Shapland et al. | 604/53 |
| 5,571,151 | 11/1996 | Gregory | 606/15 |
| 5,840,059 | 11/1998 | March et al. | 604/53 |

FOREIGN PATENT DOCUMENTS

| | | |
|---|---|---|
| 0 515 867 A2 | 12/1992 | European Pat. Off. |
| WO 96/35469 A1 | 11/1996 | WIPO |
| WO 97/47253 | 12/1997 | WIPO |
| WO 98/05307 | 2/1998 | WIPO |
| WO 98/19614 | 5/1998 | WIPO |

OTHER PUBLICATIONS

Deckelbaum, "Cardiovascular Apps. of Laser Tech.", Lasers in Surgery and Medicine, 15:315–341 (1994).

*Primary Examiner*—Hemang Sanghavi
*Attorney, Agent, or Firm*—Ray K. Shahani; Janet Kaiser Castaneda

[57] ABSTRACT

A drug delivery apparatus for dispensing a predetermined amount of one or more drugs into a laser created opening in the human body, the apparatus consisting of a laser delivery means such as an optical fiber or fiber bundle, a drug conduit which transfers the one or more drugs, drug solutions or other substances to the distal end of the laser delivery means, and the laser delivery means disposed essentially coaxially with the drug conduit. Laser delivery means is used to create a TMR channel or other opening in the body. Dispensed drug or other substance travels through the drug conduit and emanates from the drug conduit to be delivered into the TMR channel or other laser created opening. Drug is dispensed by manually or automatically activating an electric motor which actuates a piston element. A method of use is also disclosed.

38 Claims, 14 Drawing Sheets

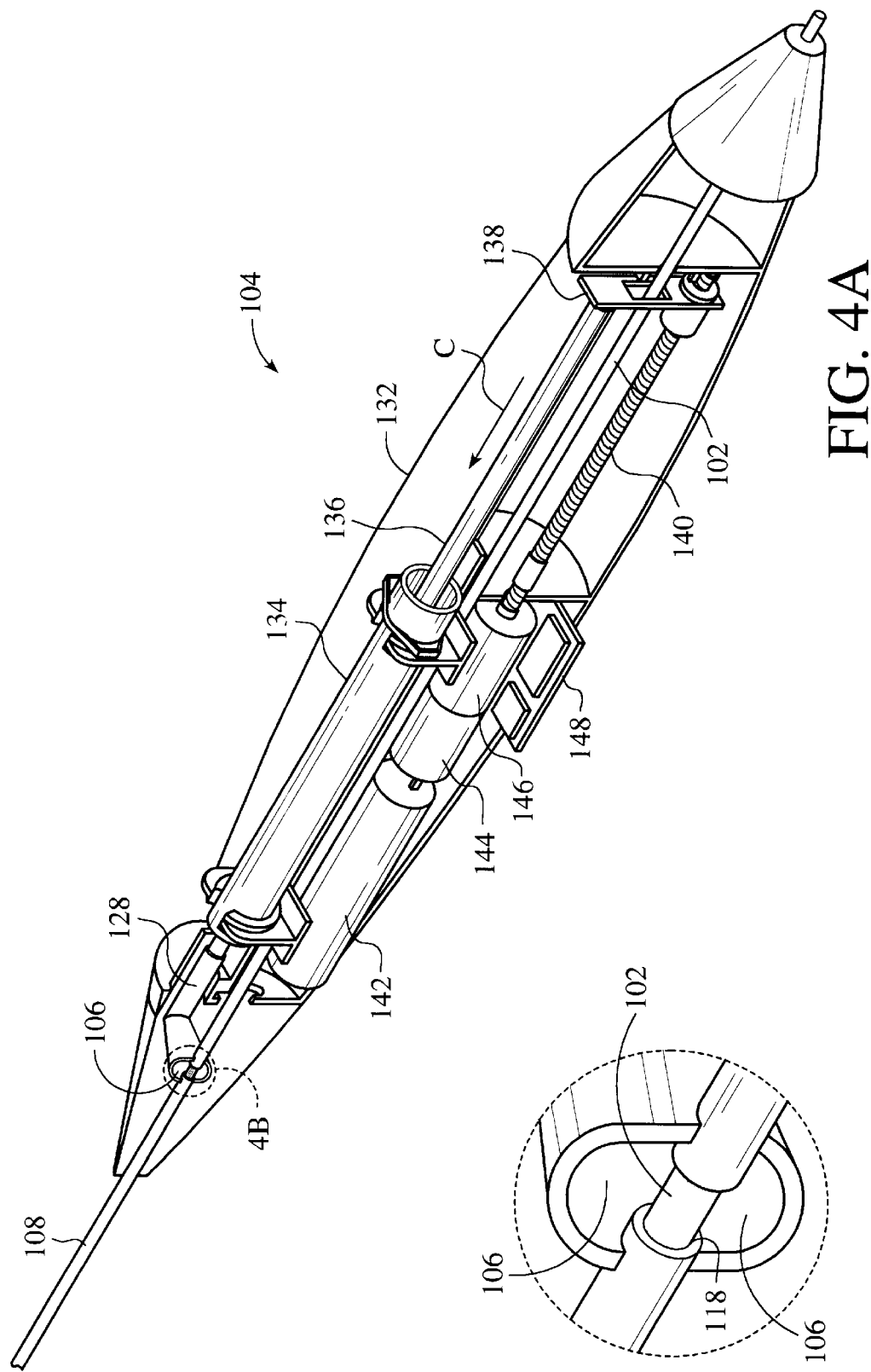

LASER DELIVERY MEANS ADAPTED FOR DRUG DELIVERY

FIELD OF THE INVENTION

The present invention relates generally apparatus and methods for delivering predetermined formulations and amounts of drugs or other materials to portions of the body with the aid of laser energy. More particularly, the invention relates to apparatus and methods for delivering predetermined formulations and amounts of drugs, medications or other materials to selected portions of tissue in conjunction with surgical and/or percutaneous procedures such as laser-assisted transmyocardial revascularization (TMR) procedures.

BACKGROUND OF THE INVENTION

In the treatment of heart disease, one method of improving myocardial blood supply is called transmyocardial revascularization (TMR), the creation of channels in the myocardium of the heart. The procedure using needles in a form of surgical "myocardial acupuncture" has been used clinically since the 1960s. Deckelbaum. L. I., Cardiovascular Applications of Laser technology, *Lasers in Surgery and Medicine* 15:315–341 (1994). It is believed that the technique relieves ischemia by allowing blood to pass from the ventricle through the channels either directly into other vessels communicating with the channels or into myocardial sinusoids which connect to the myocardial microcirculation.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures has recurred with the advent of medical lasers used to create TMR channels. Histological evidence of patent, endothelium-lined tracts within laser-created channels shows that the lumen of laser channels can become hemocompatible and remain patent. A thin zone of charring occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described in the prior art. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the surface of the heart to create the desired number of channels.

U.S. Pat. No. 5, 389,096 issued Feb. 14, 1995 to Aita et al. purports to teach one method of percutaneous TMR using an elongated flexible lasing apparatus with control lines and a focusing lens structure at the distal tip. The method describes the use of pressure to attempt to stabilize the apparatus against the wall of the heart. None of the cited TMR prior art references suggest delivery of drugs with the TMR apparatus.

In the field of drug delivery, many techniques currently exist for delivering drugs or other materials to the human body. These include, among others, oral administration, injection directly into body tissue such as through an intra-muscular injection, transcutaneous injection in which a compound is injected directly into the vasculature of a patient, or topical administration. Although many situations are satisfactorily treated by the general or directed, typically systemic acting administration of a drug, there are a great many treatments which could be facilitated and/or improved by the ability to deliver or administer a drug locally to a selected portion of a patient's body.

A recent patent, U.S. Pat. No. 5,498,238 issued Mar. 12, 1996 to Shapland et al., discloses a method of simultaneous angioplasty and drug delivery to localized portions of arteries. The patent teaches the use of an expandable balloon end type catheter which can be filled with a drug-containing fluid and which is allowed to permeate through a semi-permeable membrane of the balloon-tip end and thereby be delivered directly to the surface of arteriosclerotic lesions on stenosed arteries. However, the patent does not teach drug delivery in conjunction with any type of laser procedure nor does it contemplate such delivery with the aid of laser energy. Nor does it teach delivery of drugs or other materials directly into tissue located within portions of the body not otherwise directly accessible.

U.S. Pat. No. 5,386,837 to Sterzer discloses an "electro-chemotherapeutic" technique for treating tumors in which high intensity electromagnetic force fields (including a laser) are applied to the body after chemotherapy has been applied. This is intended to create large, transient pores in individual cells of a superficially-seated tumor lesion located between individually mounted ceramic horn antennae by non-invasively applying a highly directional beam of force-field shock of HF pulsed wave energy into the cells, thus inducing the drug to enter the cells. The patent does not, however, teach apparatus or methods for disposing such drugs or medications into the portion of the body to be treated, but instead relies on the standard approaches to chemotherapy drug delivery. The patent does not anticipate delivery of drugs to selected portions of myocardium in the heart or other internal organs of the body, but rather is directed to augmented chemotherapy to treat breast cancer and prostate cancer or benign prostatic hyperplasia (BPH).

There are a number of important problems that are not addressed by systems of the present art. None of the prior art teaches how to administer drugs from within the tissue to be treated thereby minimizing the amount of drug required, particularly for costly drugs, and also confining the drug or drugs to the particular part of the body or tissue of interest, with more importance in this regard for the administration of toxic drugs. These problems are addressed by the delivery of drugs to the tissue of internal organs, such as the heart, in conjunction with or assisted by laser energy delivery. In particular, with regard to TMR procedures, the use of laser energy combines the latest advances in the development of cardiac medications with the most advanced techniques of TMR in order to enhance and optimize treatment administered to the patient.

ADVANTAGES AND SUMMARY OF THE INVENTION

In general, this invention is directed to the delivery of drugs in any form in, near or around laser-created openings in structures including organs and other tissue within the human body, and more particularly, this invention is directed toward a system for delivering a drug directly into a channel formed in a target region of the body. The channel is created using essentially any medical laser system, particularly laser systems used in TMR procedures. While TMR procedures have been directed towards revascularization of the heart, it is understood that these principles underlying the devices and methods of use of this invention can be applied to other areas of the body. Therefore, in the context of this specification, the terms target area, target region and target surface include a patient's heart as well as any other portion of the body to which the practices of this invention can apply, including but not limited to other normal or abnormal tissue, tumors, organs, bones and muscle.

Thus, it is an advantage of the present invention to deliver drugs in all forms to laser-treated tissue.

It is a further advantage to provide an apparatus and method of use for delivering drugs to laser created channels, openings in the human body or on the surface of tissue, for instance surgical or percutaneous TMR sites, which overcome the drug delivery limitations of the prior art.

It is a further advantage of the present invention to deliver medication directly to a localized target region of the body, such as the heart, thereby enabling efficient, cost effective drug treatment and, in the case of highly toxic agents, reduction of damage to healthy tissue.

It is a further advantage of the present invention to provide a system of providing medication to tissue in which the time required for the medication to reach the tissue is reduced, inasmuch as success of such treatment in many situations depends on the medication being able to reach the tissue within a very short period of time.

Another advantage of such a system is the ability to administer a medication directly to target tissue or target areas at preselected times of delivery and rates of delivery.

Another advantage of such a system is the ability to administer saline or flushing solutions directly to target tissue or target areas at preselected times of delivery and rates of delivery.

It is a further advantage of such system to provide means to control not only the rate of delivery but also the composition of the drug or other substance solution according to a control protocol, optionally including capability to modify the administration of such drugs based on vital measurements of patient parameters such as pulse rate, blood pressure or body temperature, etc.

It is yet a further advantage of the present invention to provide a surgical or catheter apparatus which can be positioned securely adjacent a target region in a portion of the vasculature or other organ, including portions of myocardium, to be treated with drugs using laser energy.

A further advantage of the present invention is to provide such apparatus to enable drug delivery in conjunction with, i.e. before, during or after, creation of one or more laser-created openings or channels on or in selected target surfaces within the body quickly and safely.

Additionally, a more specific advantage is to provide drug delivery before, during or after laser creation of TMR channels extending through the myocardium, blind channels extending into but not through myocardium, stimulation pockets within myocardium, and other stimulation zones created using laser energy to stimulate angiogenesis.

In a preferred embodiment of the present invention, the apparatus includes a laser delivery means having one or more conduits for transmitting drugs included as a part of the delivery means. It will be understood that any suitable conventional laser delivery means, such as those known in the art and those which will be apparent from the following disclosure, will be included within the scope of the present invention. In a preferred embodiment, the conduit comprises a space along a fiber optic cable between an outer jacket of the cable and the fiber optic, or fiber optic bundle, and an aperture or array of apertures in the end of the cable through which the drug escapes into or around a newly formed channel or other opening in the target region or on a target surface. This single or plurality of apertures can be replaced with a semi-permeable or permeable membrane, strainer, set of leach holes, etc. In another embodiment, the conduit is at least one drug tube contained in the fiber bundle and the drug exits out of the target end surface of the cable. In yet another aspect, the conduit is one or more tubes between the fiber optic delivery means and the outer jacket. A piercing device may be mounted on the target end of the laser delivery means, or an optical fiber with a pointed tip which pierces the target area prior to applying the laser beam may be used. Alternatively, the distal end of the laser delivery means may include a suction cup with or without a piercing mechanism.

Several constructions are contemplated for positioning the target end of the laser delivery means for transmitting the drug. Construction of the apparatus could include, for example, in a preferred embodiment, a housing with a handle which contains one or more syringes with drug magazines which are controlled manually or automatically. Control of the transmission of drug is exercised by the operator depressing an activator to dispense drug into the conduit and associated conventional laser delivery means which extends through the housing and is extended or retracted, preferably by advance means such as by turning a thumbwheel in the housing. Adjustable parameters of such hand-held apparatus include switches, plungers or the like for activating and controlling delivery of drugs or other substances, setting aliquot dosage, repetition rate, etc.

In another aspect of the present invention, the laser delivery system is physically disassociated with the in-line drug delivery apparatus, the conventional laser delivery means of which passes through the in-line drug delivery apparatus for the addition of drugs into the conventional laser delivery means for delivery at the target tissue. In this aspect, the delivery end of the laser delivery means may, but need not necessarily, include a housing or handpiece.

Methods for performing drug delivery assisted by laser energy include piercing the target surface with a mechanical means or laser energy, and delivery of drug prior to, during or after creation of the opening using laser energy.

In a preferred method of the present invention, in a first step, a laser beam from the end of the laser delivery means creates a TMR channel or other opening in the target region. In a second step, which could be performed simultaneously with the first step, the drug or drugs are transmitted through the conduit directly into the TMR channel or other opening. In an optional step, which could either be performed prior to or simultaneously with the first and/or the second steps, the target surface, such as epicardium or endocardium, is pierced with a mechanical piercing means to provide initial access to the target region of tissue, such as myocardium.

Numerous other advantages and features of the present invention will become readily apparent from the following detailed description of the invention and the embodiments thereof, from the claims and from the accompanying drawings.

BRIEF DESCRIPTION OF THE DRAWINGS

The foregoing and still other advantages of the present invention will be more apparent from the following detailed explanation of the preferred embodiments of the invention in connection with the accompanying drawings wherein:

FIG. 4A is a representative isometric view of a preferred embodiment of an in-line drug delivery apparatus adapted for addition of drug to the cable of the laser delivery means, which cable extends through the drug delivery apparatus of the present invention.

FIG. 4B is a partial detail view of the drug reservoir and manifold showing addition of drug from the drug reservoir to the fiber cable.

DETAILED DESCRIPTION OF THE PREFERRED EMBODIMENT

Scope of Drug Delivery

Figure 1:
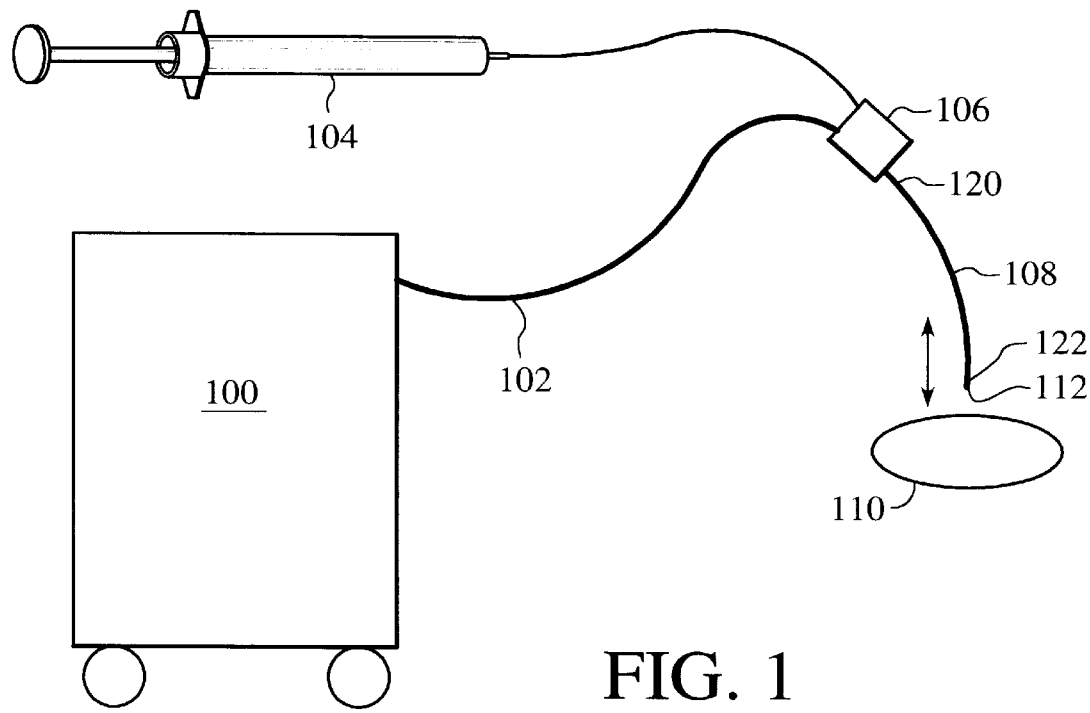
FIG. 1 is a representative schematic view of a preferred embodiment of the method of use of a drug delivery apparatus of the present invention.

The concept of drug delivery includes any application where a drug or other substance is delivered in the area of laser treatment. This invention relates generally to the topic of drug delivery with laser delivery devices, and more particularly to drug delivery in conjunction with TMR in which, for example, antiarrhythmic drugs, growth factors or other drugs or compounds can be delivered to the heart during the TMR procedure.

For the purposes of the present invention and disclosure herein, the term "drug" or "drugs" includes any and all drugs which could or will be used in the manners described herein, including and not limited to the compounds named in the following tables, other medications, antibiotics, vaccines, function regulators, other materials for performing functions including flushing and cooling, stimulating other responses, detection, analysis, monitoring, visualization or control, etc., said solutions comprising waters, saline and the like, solid and semi-solid materials, and in any forms including capsules and granules, implants, etc.

The present invention includes the delivery of liquid, solid or semi-solid, time release formulations, etc. It is important to consider that a large local concentration of drug may result, particularly in the case of when a solid dissolves in fluid or tissue and becomes bioavailable, unless the particular drugs or other substances being delivered are fairly insoluble or are otherwise formulated to dissolve slowly enough to avoid unacceptably high concentrations, locally or elsewhere. Care must also be taken to avoid solid materials drifting or migrating from the area of intended treatment, such as by implantation, transdermal application, etc.

Preferred parameters for drug delivery in conjunction through a laser catheter provide a single, acute or multiple acute or sustained administration of the drug to produce a therapeutic effect. Additionally, for certain drug systems, drug half-life should be consistent with the clearance mechanisms present in the environment where the drug is introduced. Drugs that need frequently repeated administration over longer periods of time could require repeated hospitalizations or clinic visits—an exception to this is in the case of cancer chemotherapy, where the patient normally goes to the hospital for drug administration in the course of routine treatment. In the case of a drug administered with TMR, where blood circulation may cause a rapid clearance of any therapeutic delivered in or near the channels, the drug would need a time course of action that is rapid enough to have effect before it is cleared.

One set of applications of such drug delivery in conjunction with laser procedures involve certain antibody treatments, where it is desirable to target the antibody to the area of intended treatment in order to achieve the highest possible local concentration of a relatively extremely expensive reagent. For example, in enzyme-linked antibody therapy currently under investigation in the treatment of certain cancers, an enzyme linked to an antibody specific to a tumor is delivered and allowed to bind to the tumor cells.

Thus, at present the two main applications for which laser assisted drug delivery would be advantageous are (1) delivery of angiogenic factors in conjunction with TMR and (2) delivery of a chemotherapeutic to a solid tumor after a laser is used to ablate tumor tissue. A normally toxic chemotherapeutic such as doxorubicin or taxol that is made systemically non-toxic by being modified to a prodrug is injected into the tumor. The drug would remain non-toxic until it meets the enzyme linked to the antibody, where the prodrug is converted into active drug. In this way, higher local concentrations of the drug could be created near the tumor than would be possible by traditional chemotherapy, where systemic toxicity is the limiting factor.

Scope of Drug Therapy

Therapeutics which may be advantageous to deliver through a laser/catheter device can be broadly placed into four overlapping therapeutic categories:

1) agents which act on the blood clot cascade,
2) agents that mediate inflammation or cell adhesion/recognition processes,
3) agents which have an effect on the cardiovascular system, and
4) agents that may be used in the treatment of cancer.

These categories are broadly overlapping, so that many agents will fall into more than one category. Antibody agents, for example, will appear in all four categories. Certain growth inhibitors can be used for anti-cancer treatment as well as for the treatment of other disease processes. Agents named in the following charts are illustrative and are not meant to be a comprehensive listing of all agents available for the given therapeutic category. Agents appearing as examples in one category may have uses in other therapeutic categories.

It will be understood that there are additional categories which may become useful, such as agents which are directed at bone, agents implanted in semi-permeable sacs, radioisotopes, and future gene therapies.

Photodynamic therapy is another important delivery and dosing method. Drugs or other compounds which have certain therapeutic or other activity or function can be regulated using such technology. Photo-active or photo-labile compounds are those whose activity or function is controlled by light energy. While the use of sensitizing agents or protective groups to block activity of the drug or other compounds in topically applied formulations is known, the use of such protective groups is unknown in conjunction with drugs delivered for angiogenic purposes or in conjunction with TMR.

"Caged" compounds are compounds which have a photoactive reagent which masks the original characteristics of the compounds. Thus, these caged or otherwise photo-labile compounds can be delivered to the target tissue or target region in a pharmacologically in-active form. Upon irradiation with laser energy or other, operative electromagnetic radiation, the protective group or groups are caused to be rendered inert, thereby initiating therapeutic activity. These photoactive protective groups or "cage" molecules are especially useful in conjunction with highly toxic drugs or marker substances. For example, chemotherapeutic agents are particularly toxic and, thus, their toxicity can be eliminated until the agent is delivered to the precise region of the body where it's toxicity will be most effectively and safely used. Irradiation of the photo-labile compound with light energy of a suitable wavelength, frequency and duration can then render the drug or other photo-labile agent active.

Dosing

Active compounds which are given systemically have a normal therapeutic window which can be expressed as mg of drug per kg of body weight. The amount of agent which is therapeutically acceptable when administering a drug locally can be approximated as mg of drug per kg of target treatment area (e.g. organ weight), optimized accordingly with consideration of toxicity and mechanism of drug action.

Agents delivered to a specific site can achieve high local concentrations at the delivery point. Optimal drug dose may scale differently when the drug is administered locally rather than systemically. Thus, the amount of a given agent that should be delivered in order to achieve a therapeutic effect must be optimized accordingly with consideration of toxicity levels (both locally and systemically), mechanism of drug action, drug clearance mechanisms, and drug diffusion levels.

Category 1—Examples of Agents Which Have an Effect on the Blood Clot Cascade

These agents work by either promoting or inhibiting blood clot cascade pathways. These agents are actual blood clot cascade participants, which mimic actual blot clot cascade participants, or agents which act as enzymes or inhibit enzymes that are associated with the blood clot cascade. Some examples of agents in these categories include:

| Category | Agent | Manufacturer | Indication | Form |
|---|---|---|---|---|
| Anticoagulant Antagonists | Protamine Sulfate | Eli Lilly | treatment of heparin overdosage | IV |
| Anticoagulants | Heparin | Wyeth-Ayerst | prophylaxis and treatment of venous thrombosis; prevention of post-operative deep venous thrombosis and pulmonary embolism; prevention of clotting in arterial and cardiac surgery; prophylaxis and treatment of peripheral arterial embolism | IV |
| Antifibrinolytic | Amicar (aminocapro ic acid) | Immunex | enhances hemostasis when fibrinolysis contributes to bleeding | IV/oral |
| Platelet Inhibitors | ReoPro (abciximab) | Eli Lilly | adjunct to percutaneous transluminal coronary angioplasty or atherectomy (PTCA) for the prevention of acute cardiac ischemic complications in patients at high risk for abrupt closure of the treated coronary vessel | IV |
| Throm- | Acti- | Genentech | management of acute | IV |

-continued

| Category | Agent | Manufacturer | Indication | Form |
|---|---|---|---|---|
| bolytics | vase (alteplase, TPA) | | myocardial infarction in adults, management of acute massive pulmonary embolism in adults | |

Category 2—Examples of Agents That Mediate Cell Adhesion and/or Cell Recognition Processes These agents act on cell signaling pathways and recognition processes, and includes receptor agonists and antagonists. A subset of these agents mediate inflammation and the immune response. Some examples of agents in the category include:

| Category | Agent | Manufacturer | Indication | Form |
|---|---|---|---|---|
| Antihistamines | Seldane (terfenadine) | Marion Merrell Dow | relief of symptoms associated with seasonal allergic rhinitis | oral |
| Anti-Inflammatory Agents | Toradol (ketorolac tromethamine) | Roche Laboratories | short-term (<5 days) management of moderately severe, acute pain that requires analgesia at the opioid level | IV/ IM/ oral |
| Immunosuppresives | Sand-immune (cyclosporin) | Sandoz | prophylaxis of organ rejection in kidney, liver, and heart allogeneic transplants; also in the treatment of chronic rejection in patients previously treated with other immunosuppresive agents | IV/ oral |
| Receptor Antagonists | Tagamet (cimetidine hydrochloride) | Smith-Kline Beecham | management of ulcers, erosive gastroesophageal reflux disease prevention of upper gastrointestinal bleeding in critically ill patients, treatment of pathological hypersecretory conditions | IV/ IM/ oral |

Category 3—Examples of Cardiovascular Agents

These agents work at various points in the cardiovascular and associated systems. Angiogenic factors and anti-angiogenic factors appear in this category as well as in the cancer therapeutics category. Some examples of agents in the category include:

| Category | Agent Name | Manufacturer | Indication | Form |
|---|---|---|---|---|
| Adrenergic Blockers | Minipress (prazosin hydrochloride) | Pfizer | treatment of hypertension | oral |
| Adrenergic Stimulants | Aldomet (methyldopate HCl) | Merck | treatment of hypertensive crisis | IV |
| Alpha/Beta Adrenergic Blockers | Normodyne (labetalol HCl) | Schering | control of blood pressure in severe hypertension | IV |
| Angiotensin Converting Enzyme Inhibitors | Capoten (captopril) | Bristol-Myers Squibb | treatment of hypertension | oral |
| Angiotensin II Receptor Antagonists | Cozaar (losartan potassium) | Merck | treatment of hypertension | oral |
| Antiarrhythmics Group I | Norpace (disopyramide phosphate) | Searle | treatment of documented ventricular arrhythmias, such as sustained ventricular tachycardia | oral |
| Antiarrhythmics Group II | Brevibloc (esmolol hydrochloride) | Ohmeda | rapid control of ventricular rate in patients with atrial fibrillation or atrial flutter in perioperative, postoperative, or other emergent circumstances where short term control of ventricular rate with a short-acting agent is desired; indicated in noncompensatory sinus tachycardia where the rapid heart rate requires specific intervention; indicated of the treatment of tachycardia and hypertension that occur during inuction and tracheal intubation, during surgery, on emergence from anesthesia, and in the postoperative period | IV |
| Antiarrhythmics Group III | Cordarone (amiodarone HCl) | Wyeth-Ayerst | treatment and prophylaxis of frequently recurring ventricular fibrillation and hemodynamically unstable ventricular tachycardia in patients refractory to other therapy | IV/ oral |
| Antiarrhythmics Group IV | Cardizem (diltiazem HCl) | Marion Merrell Dow | IV: indicated for atrial fibrillation or atrial flutter and paroxysmal supraventricular tachycardia oral: treatment of hypertension and management of chronic stable angina and angina due to coronary artery spasm | IV/ oral |
| Beta Blockers | Inderal (propranolol HCl) | Wyeth-Ayerst | management of hypertension, management of angina pectoris due to coronary atherosclerosis, management of cardiac arrhythmias, indicated to reduce cardiovascular mortality in patients who have survived the acute phase of myocardial infarction and are clinically stable, prophylaxis of the common migraine headache | IV/ oral |
| Calcium Channel Blockers | Procardia (nifedipine) | Pratt Pharmaceuticals | management of vasospastic angina, chronic stable angina, and hypertension | oral |

-continued

| Category | Agent Name | Manufacturer | Indication | Form |
|---|---|---|---|---|
| Diuretics | Burnex (bumeta-nide) | Roche | treatment of edema associated with congestive heart failure, hepatic and renal disease, including nephrotic syndrome | IV/IM/oral |
| Hypertensive Emergency Agents | Hyperstat (diazoxide) | Schering | short-term use in the emergency reduction of blood pressure in severe, non-malignant and malignant hypertension | IV |
| Growth Factors | Vascular Endothelial Growth Factor (VEGF) (preclinical) | Genentech | promotes angiogenesis; still experimental | preclinical |
| Inotropic Agents | Lanoxin (digoxin) | Glaxo Wellcome | management of heart failure, atrial fibrillation, atrial flutter, paroxysmal atrial tachycardia | IV/oral |
| Patent Ductus Arteriosus Therapy | Indocin (indomethacin sodium trihydrate) | Merck | indicated to close a hemodynamically significant patent ductus arteriosus in premature infants | IV |
| Rauwolfia Derivatives & Combinations | Diupres (reserpine-chlorothiazide) | Merck | hypertension | oral |
| Vasodilators | Nitrostat (nitroglycerin) | Parke-Davis | prophylaxis, treatment, and management of patients with angina pectoris | oral |
| Vasopressors | Vasoxyl (methoxamine hydrochloride) | Glaxo Wellcome | supporting, restoring, or maintaining blood pressure during anesthesia | IV |

Category 4—Examples of Cancer Therapeutics

Cancer therapy can proceed along several different lines, all of which seek to kill or limit the growth of cancer cells while doing minimal damage to the host. Thus, any difference in cancer cell properties (e.g. metabolism, cell-surface antigen presentation) from healthy host cells is a target for exploitation. With the local administration of therapeutics, these differentiating factors may be created and/or exploited. For example, the local administration of cytotoxins or growth inhibitors may allow higher local concentrations of the compounds than would be achievable by systemic administration. Differences in cell-surface recognition molecules may be a site for antibody therapy. Differences in tumor morphology are also potential sites of intervention: for example, anti-VEGF may be useful in retarding the vascularization of the interior of a solid tumor, thereby slowing its growth rate. Some examples of agents in the category include:

| Category | Agent Name | Manufacturer | Indication | Form |
|---|---|---|---|---|
| Adjuncts | Kytril (granisetron HCI) | Smith-Kline Beecham | prevention of nausea and vomiting associated with emetogenic cancer therapy, including high-dose cisplatin | IV |
| Androgen Inhibitors | Lupron (leuprolide acetate) | TAP Pharmaceuticals | palliative treatment of prostatic cancer | IM |
| Antibiotic Derivatives | Doxorubicin Hydrochloride | Astra USA | produces regression in disseminated neoplastic conditions and possibly some solid tumors | IV |
| Antiestrogen | Nolvadex (tamoxifen citrate) | Zeneca Pharmaceuticals | treatment of metastatic breast cancer | oral |
| Antimetabolites | Roferon-A (interferon alfa-2a) | Roche | treatment of hairy cell leukemia and AIDS-related Kaposi's sarcoma | IM/SC |
| Cytotoxic Agents | Taxol | Bristol-Myers Squibb | treatment of metastatic carcinoma of the ovary and treatment of breast cancer | IV |
| Enzyme Inhibitors | Ras farnesyl-transferase inhibitor (preclinical) | Genentech | treatment of pancreatic and colon cancers | preclinical |
| Hormones | Depo-Provera (medroxy-progesterone acetate) | Upjohn | adjunctive therapy and palliative treatment of inoperable, recurrent, and metastatic endometrial or renal carcinoma | IV |
| Immunomodulators | Proleukin (aldesleukin) | Chiron | treatment of metastatic renal cell carcinoma | IV |
| Nitrogen Mustard Derivatives | Alkeran (melphalan HCI) | Glaxo Wellcome | treatment of multiple myeloma | IV/oral |

TMR and Angiogenic Factors

TMR is based on the theory that blood will flow directly from the left ventricle into the channels and then into the myocardial vascular plexus. Although the mechanism of TMR is still being investigated, there is some indication that the channels remain patent for a significant period of time following their creation. There is a question of whether blood washing in and out of the channels and the attendant diffusion into the muscle provides an adequate oxygen supply to the myocardium. The possibility exists that since TMR induces some secondary vascularization, whatever signal is given to induce vascularization could be pharmacologically amplified. Mechanisms for this type of induced revascularization may stem from factors induced by tissue damage (VEGF or other growth-factor derived response, or perhaps heat-shock proteins produced by thermal damage caused by the laser). Regardless of the actual mechanism, an angiogenic factor used in conjunction with TMR may increase the effectiveness of the technique.

A preferred one of the angiogenic factors commonly available (e.g. VEGF, FGF-1, FGF-2, EGF) is VEGF, vascular endothelial growth factor. VEGF has been shown to be effective in improving vascularization in the rabbit ischemic hindlimb model after a single bolus administration. VEGF also has a serum half life of less than 6 minutes (unpublished results), and certain isoforms of VEGF have the property to bind to the cell surface—i.e. VEGF may not need to be present for very long in order to have an effect. Thus, it is possible to apply VEGF in or near TMR channels to increase the revascularization of ischemic myocardium.

If the cause of ischemia is a constriction of blood supply upstream from the capillary bed, then VEGF therapy alone will not be shown to be as effective as TMR alone. Angiogenesis produced by VEGF in the myocardium may have limited effectiveness when the cause of ischemia is occlusion of coronary arteries: this limits the amount of blood available to the myocardium. The advantage of a TMR/VEGF combination treatment is that the transmural channels created in TMR could provide a source of blood to the newly vascularized myocardium that is otherwise unavailable.

Basic fibroblast growth factor (bFGF), also known as FGF-2, is another possible agent. There is some indication that VEGF and bFGF used together are more effective than either one alone.

Laser Delivery Means Adapted for In-Line Drug Delivery Apparatus

For purposes of clarity, identical reference numerals are used throughout the accompanying drawings, corresponding to structurally and/or functionally similar elements of the invention disclosed herein.

FIG. 1 is a representative schematic view of a preferred embodiment of a drug delivery apparatus of the present invention. A laser source 100 provides laser energy. Laser energy is delivered via laser delivery means 102. It will be understood that said laser delivery means 102 can be any suitable laser delivery means including individual optical fibers, bundles of optical fibers, cables, rods, articulating arms or other devices known to those skilled in the art. The laser delivery means adapted for drug delivery apparatus 104 dispenses one or more drugs, drug solutions, solids, or other substances such as saline, flushing or cooling solutions from a drug reservoir 134 contained therein, as shown in FIG. 4A, via manifold 106 to drug conduit 108. The drug conduit 108 contains drugs to be delivered to the target tissue 110 in conjunction with the laser delivery means 102. In preferred embodiments, as described in greater detail below, drug conduit 108 comprises a leach tube, or end tube(s), or other means for delivering the drug(s) dispensed by the laser delivery means adapted for drug delivery apparatus 104 preferably in the region of the distal end 112 of the laser delivery means 102. FIG. 1 is schematic and representative only, and the invention encompasses delivery of more than one drug(s) and/or other substances via a manifold which associates the drug or other substances with the laser delivery means located at any place within the physician's armamentarium.

Figure 2A:
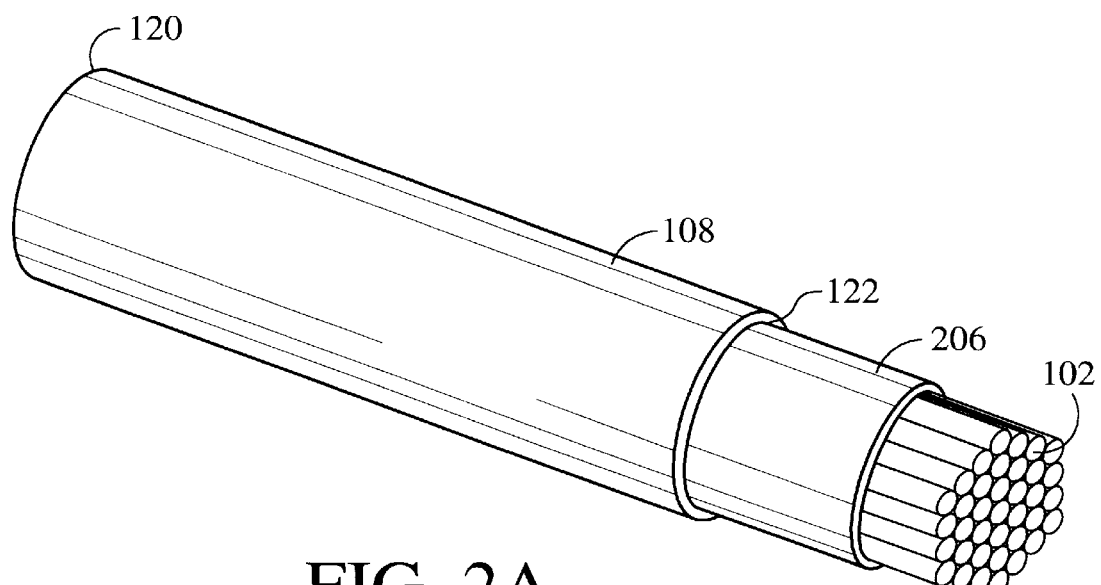
FIGS. 2A–2C are representative perspective, side and cross section views of a preferred embodiment of the laser delivery means adapted for drug delivery apparatus of the present invention.
Figure 2B:
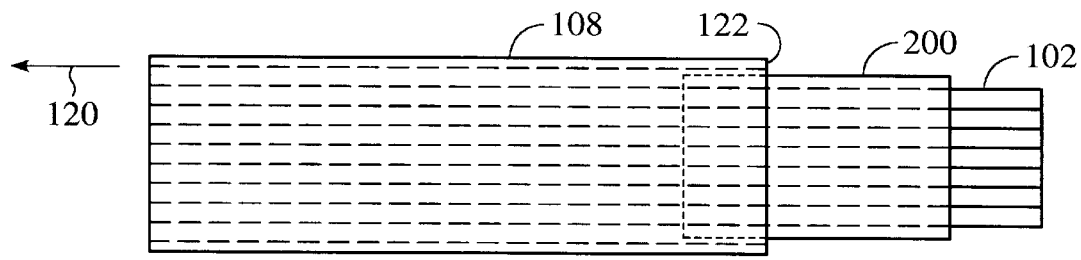
Figure 2C:
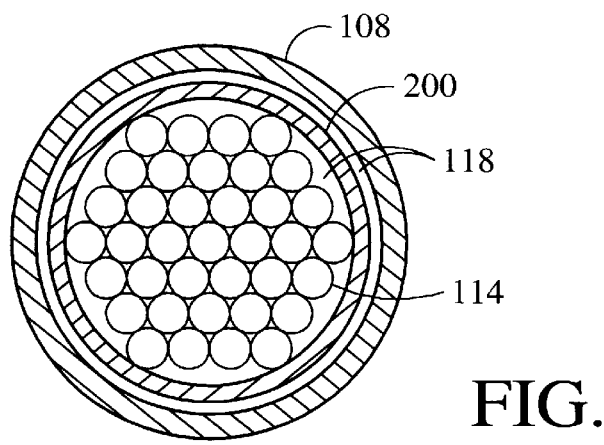

FIGS. 2A–2C are representative perspective, side and cross section views of a preferred embodiment of the laser delivery means adapted for drug delivery apparatus of the present invention. The distal end 112 of the laser delivery means 102 will preferably be disposed within the drug conduit 108 distal to the manifold 106. A proximal end 120 of the drug conduit 108 is located adjacent the manifold 106. Drugs are communicated from the drug delivery apparatus 104 and pass into drug conduit 108. The drug conduit 108 portion of the embodiment can be made of any suitable material, including but not limited in any way to high density, polypropylene, "crystal-flex" type tubing. Its manufacture and diameter will be dependent upon the type of laser delivery means 102 being used, i.e., single fiber, fiber bundle, waveguide, rod, or waveguide or cable carried within an articulating arm, etc.

A tantalum band 200 or other marking device may be placed at the end of the apparatus adjacent the distal end 112 of the laser delivery means 102. It will be understood that the tantalum band 200 serves to make the distal end 112 of the laser delivery means 102 radio opaque for visualization. A wide variety of other visualization-enhancing attachments or materials of construction may be used in various ways and are all considered within the scope of this invention.

Drug will flow or otherwise be transferred through a drug channel 118, formed by the space between the inner wall surface of the drug conduit 108 and the laser delivery cable 102, passing into or around a laser created opening through the distal end 122 of the drug conduit 108.

FIGS. 3A–3D are representative side, cross section and detail views of a preferred embodiment of the leach tube embodiment of a laser delivery means adapted for drug delivery apparatus of the present invention. The laser delivery means 102 will be disposed within the drug conduit 108. The distal end 122 of the drug conduit 108 forms the leach tube embodiment—a plurality of (i.e. one or more) perforations 124 formed through the wall of drug conduit 108 allow drugs in space 118 to flow or otherwise be transmitted through drug conduit 108.

The distal end 112 of the laser delivery means 102 preferably extends past the distal end 122 of the drug conduit 108. As shown, a preferred type of laser delivery means 102 consists of a bundle of individual optical fibers 114. It will be understood that, in the case of a fiber bundle, the outer jacket 116 will also contain an epoxy or other polymeric or other suitable material for "potting" the fiber bundle. This potting material will serve to hold the fibers in place relative to each other and the outer jacket 116.

Outer jacket 116, such as a thin plastic tubing material, surrounds the bundle of individual fibers 114, and serves to hold them together in an operative arrangement. This outer jacket 116 will also serve to reflect any light leaks from the fibers back into the fibers, or at least out the distal end 112 of the laser delivery means 102. Thus, the combination of outer jacket 116 and drug conduit 108 defines an interstitial drug channel 118 through which drugs can be conveyed from the manifold 106 through conduit 108 and out the plurality of perforations 124. It will be understood that the outer jacket 116 is optional and may be omitted. In such case, utilizing a single fiber mounted within conduit 108 will result in drug delivery from the plurality of perforations 124 in essentially the same manner as described above. However, in the case of a bundle of fibers without a outer jacket 116, drug solution or other substances will flow from the manifold 106 around each of the individual fibers 114 of the bundle, thus resulting in percolation of drug out of the drug conduit 108 at either or both the plurality of perforations 124 and the distal end 112 of the fiber bundle.

In the embodiments shown, individual perforations 124 are spaced about outer jacket 116. It will be understood that more or fewer perforations may be used, and perforations located at various axial positions located adjacent the distal end 122 of the drug conduit 108. The perforations 124 could be replaced with a portion of permeable or semi-permeable material to controllably deliver drug solution or other substances therefrom.

Figure 3A:
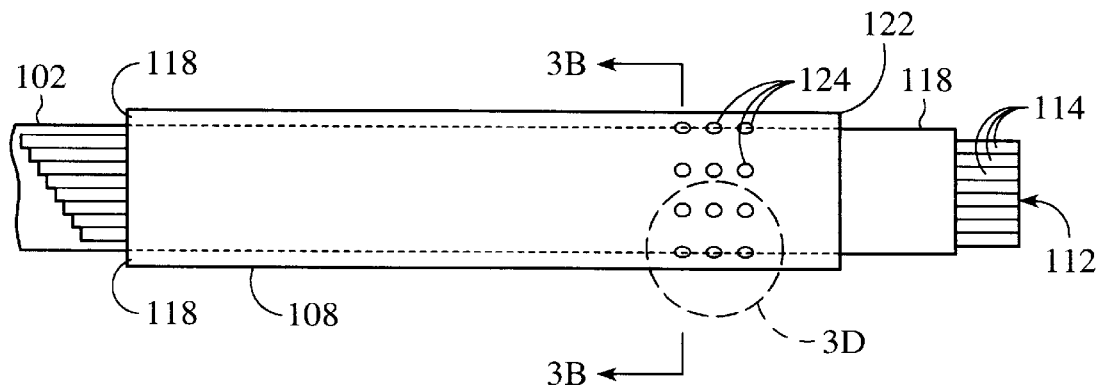
FIGS. 3A–3D are representative side, cross section and detail views of a preferred embodiment of the leach tube embodiment of a laser delivery means adapted for drug delivery apparatus of the present invention.
Figure 3B:
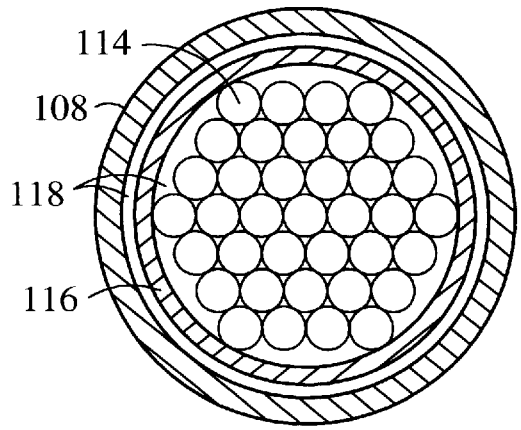
Figure 3C:
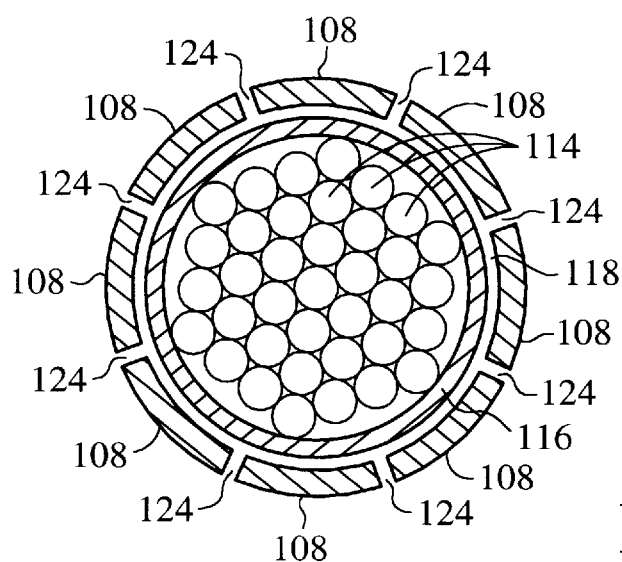
Figure 3D:
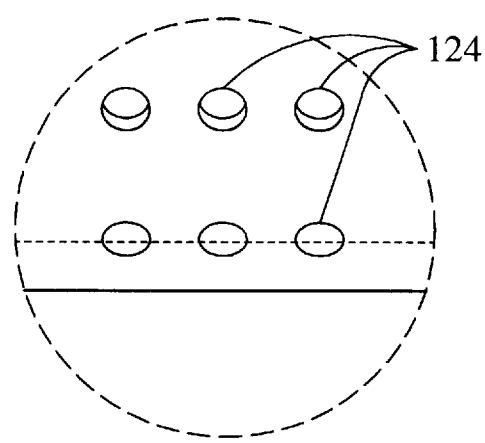
Figure 3E:
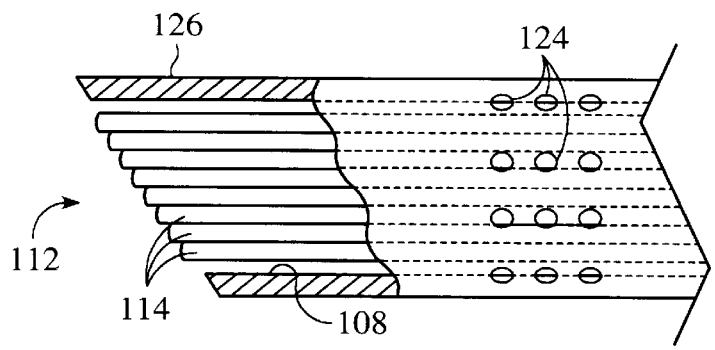
FIG. 3E is a representative plan view of another preferred embodiment of the leach tube embodiment and laser delivery means adapted for drug delivery apparatus of the present invention.

FIG. 3E is a representative plan view of another preferred embodiment of the leach tube embodiment and laser delivery means adapted for drug delivery apparatus of the present invention. In this embodiment, the laser delivery means 102 comprises a bundle of individual optical fibers 114 each cleaved or otherwise positioned adjacent each other, having a distal end 112 formed with an angle cut piercing tip 126. It will be understood that this piercing tip 126 can be either formed integral with the drug conduit 108 or it can be formed by the outer jacket 116 and/or marking band 200 at the distal end 112 of the laser delivery means 102 itself. This piercing tip can be formed from the same material as used for the drug conduit 108 or fiber outer jacket 116. It will be understood that when employing either a percutaneous approach or a surgical approach, a piercing tip 126 at the distal end 112 of the laser delivery means 102 can be used initially to pierce a surface of the target area. In the case of surgical TMR, this will minimize bleeding from the epicardium, stabilize the device in the tissue, improve visibility in the region and reduce the incidence of adhesions between the epicardial surface and the pericardial sac. Furthermore, in a catheter assembly used in a vascular approach, an optional piercing device or means will stabilize the device. Then, advancing or retracting a fiber or other laser delivery means a predetermined distance into or out of myocardium while delivering laser energy will create an opening, such as a TMR channel or other treatment site, for delivery of drugs therein.

Figure 3F:
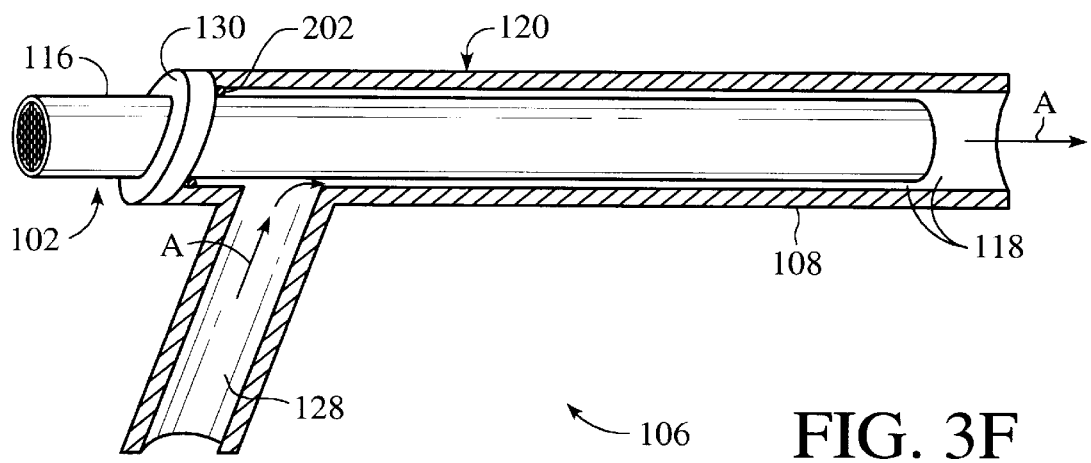
FIG. 3F is a representative section view of a preferred embodiment of a manifold associated with the leach tube embodiment of a laser delivery means adapted for drug delivery apparatus of the present invention.

FIG. 3F is a representative section view of a preferred embodiment of a manifold 106 associated with a laser delivery means adapted for drug delivery apparatus of the present invention. This representative view of the manifold 106 is shown with an optical fiber bundle or other laser delivery means 102. Drug is introduced to the manifold 106 through one or more drug ports 128. The laser delivery means 102 enters the manifold at laser delivery means port 130. Both of the ports are located at the proximal end 120 of the drug conduit 108. The drug channel 118 extends from the proximal end 120 of the drug conduit 108 through to the distal end 122 of conduit 108. Seal means 202 will prevent backflow through conduit means 108 of drug, solutions or other substances.

Figure 3G:
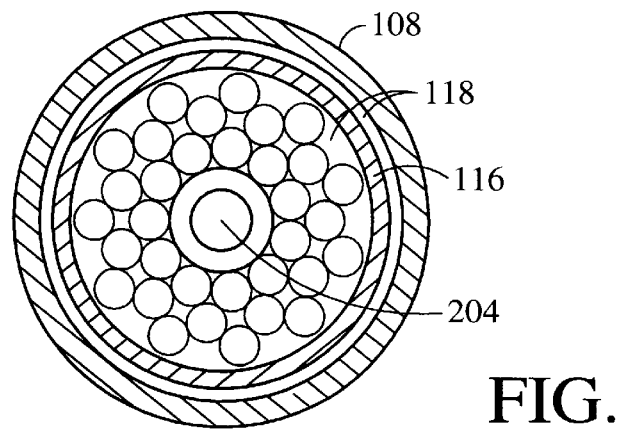
FIG. 3G is a representative cross section view of a preferred embodiment of a laser delivery means with infusion tube adapted for drug delivery apparatus of the present invention.

FIG. 3G is a representative cross section view of a preferred embodiment of a laser delivery means with infusion tube 204 adapted for drug delivery apparatus of the present invention. In this embodiment, the infusion tube 204 is an appropriately sized tube made of drug and other substance-compatible material, e.g. teflon. Infusion tube 204 extends from the manifold 106 (not shown) at which point it receives the drug being transmitted therethrough through its proximal end (not shown), to its distal end 206 at or near the distal end 112 of the laser delivery means 102. It will be understood, additionally, that a plurality of perforations in an optional conduit 108 also would allow infusion of drug from drug channel 118 through optional leach holes or at the distal ends of the individual fibers 114 of the laser delivery means 102 if so desired. Preferably, the distal end of the infusion tube 204 terminates in essentially the same plane as defined by the distal end faces of the individual fibers 114 of laser delivery means 102.

Figure 3H:
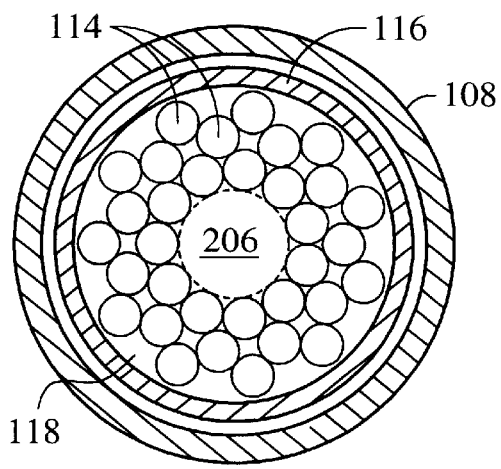
FIG. 3H is a representative cross section view of a preferred embodiment of a laser delivery means with an infusion channel adapted for drug delivery apparatus of the present invention.

FIG. 3H is a representative cross section view of a preferred embodiment of a laser delivery means with an infusion channel 206 adapted for drug delivery apparatus of the present invention. In this embodiment, it will be understood that an optional drug channel 118, as defined above, may also be provided.

Figure 3I:
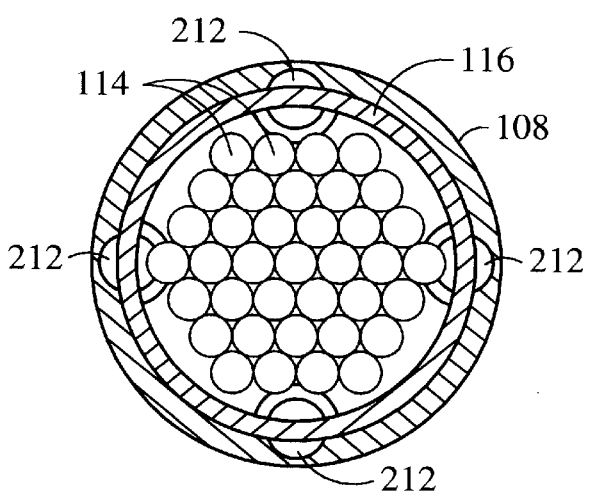
FIG. 3I is a representative cross section view of a preferred embodiment of a laser delivery means with multi lumen drug conduits adapted for drug delivery apparatus of the present invention.

FIG. 3I is a representative cross section view of a preferred embodiment of a laser delivery means with a multi lumen drug conduit adapted for drug delivery apparatus of the present invention. A plurality of lumens 212 extend from the proximal end 120 of the drug conduit 108 along the length of the drug conduit to its distal end 122. It will be understood that these plurality of lumens 212 can be individual elongated tubes placed within the laser delivery means 102 or adjacent to the laser delivery means 102. In a preferred embodiment, the plurality of lumens 212 can be formed integrally with the drug conduit 108. As described above, the plurality of lumens 212 thereby provide one or more individual drug channels 118 communicating drug therethrough.

Figure 3J:
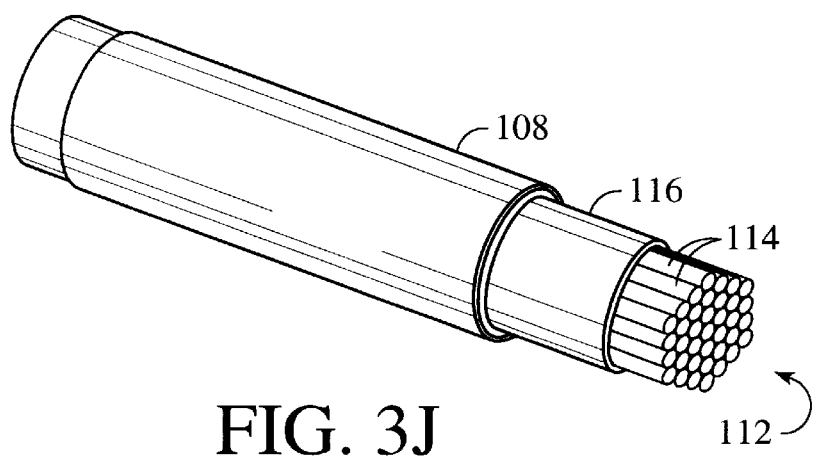
FIG. 3J is a representative perspective view of a preferred embodiment of a laser delivery means with diffusion strip adapted for drug delivery apparatus of the present invention.

FIG. 3J is a representative perspective view of a preferred embodiment of a laser delivery means with diffusion strip adapted for drug delivery apparatus of the present invention. In this embodiment, a drug or other substance 214 is affixed directly to the distal end 112 of laser delivery means 102. It will be understood that the drug or other substance 214 can be a solid material or other material placed on an adhesive backed layer to enable fixation of the drug or other substance 214 to the distal end of laser delivery means. In this embodiment, delivery of the drug or other substance 214 is achieved by creation of an opening in the target tissue by the distal end 112 of laser delivery means 102 and diffusion of the drug or substance 214 into the surrounding tissue in contact with the drug.

Figure 3K:
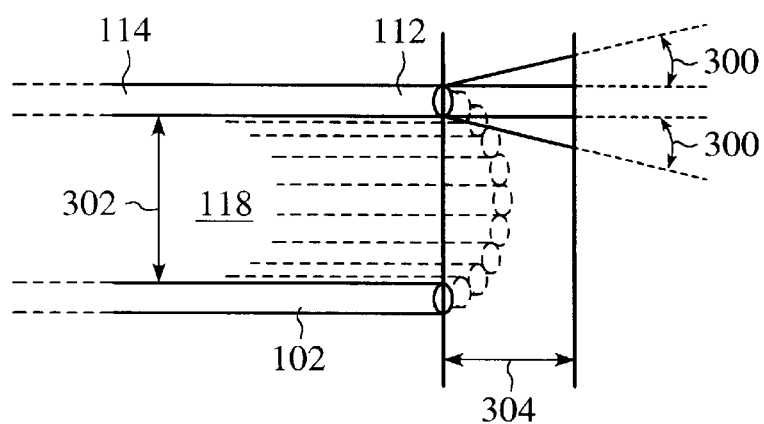
FIG. 3K is a representative view of a preferred embodiment of the distal end of a laser delivery means adapted for drug delivery of the present invention.

FIG. 3K is a representative view of a preferred embodiment of the distal end 112 of a laser delivery means 102 adapted for drug delivery of the present invention. It will be understood that the hollow opening or drug channel 118 is formed by a plurality of individual optical fibers 114 arranged in a bundle or otherwise. Mathematically, it is possible to determine the range, depth, time, etc. of ablation using specific optical fibers, specific diameters, etc. For example, and not to be construed as limiting in any way, assuming a full pack of 1 millimeter fibers ablates about 1 millimeter deep per pulse of energy (say at about 2.5 Joules per pulse). Given a certain divergence angle 300, for example between about 11 and about 14 degrees, one could calculate an operative range of diameters 302 which would provide ablation at a certain distance 304 from the distal end 112 of the laser delivery means 102, as desired.

In-Line Drug Delivery Apparatus

Figure 5:
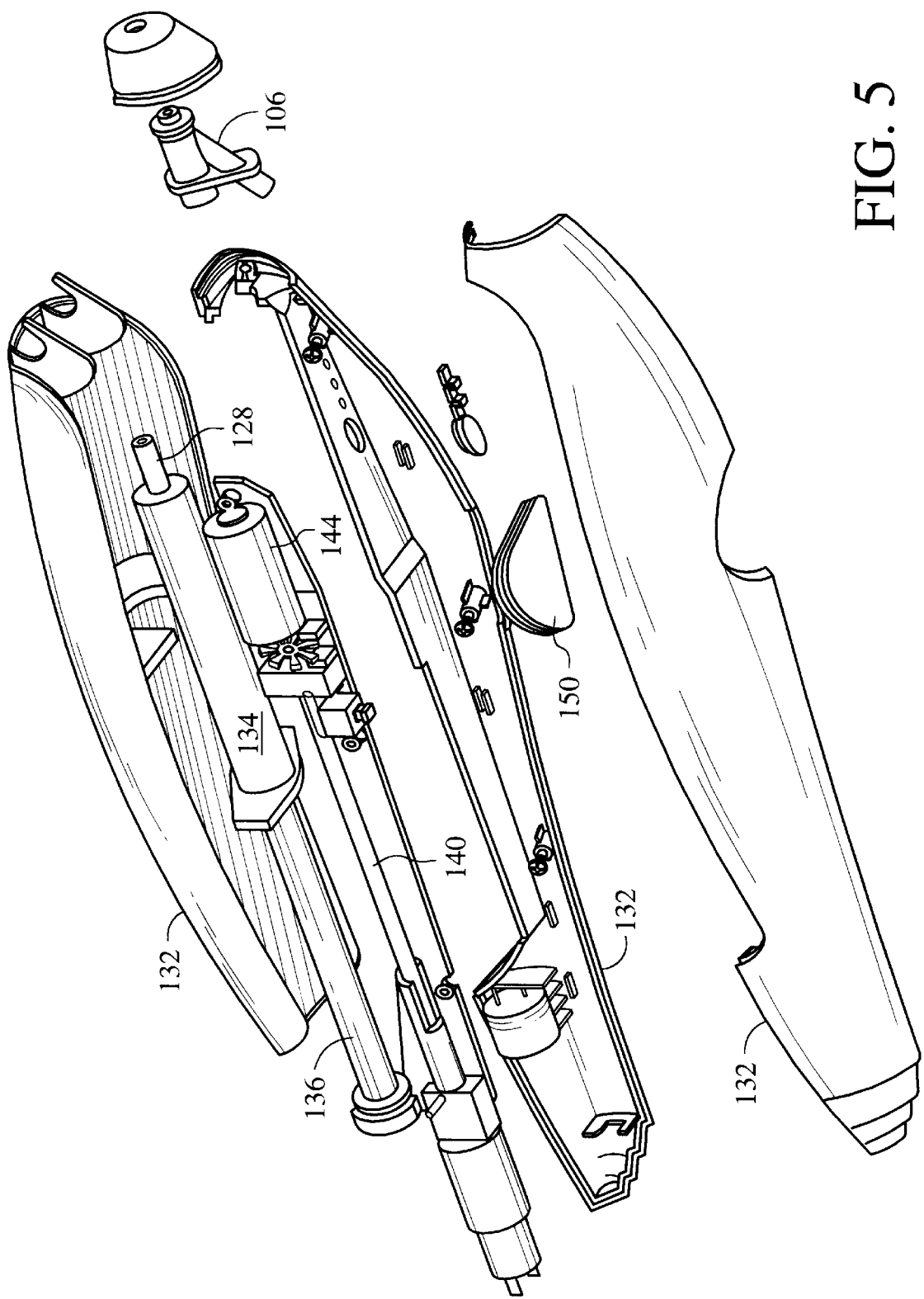
FIG. 5 is a representative exploded view of a preferred embodiment of an in-line drug delivery apparatus of the present invention.

FIG. 4A is a representative isometric view of a preferred embodiment of an in-line drug delivery apparatus for dispensing drug into the conduits described above where the laser delivery cable passes through the drug delivery apparatus itself. FIG. 4B is a partial detail view of the manifold of a preferred embodiment. FIG. 5 is a representative exploded view of an in-line drug delivery apparatus of the present invention. All of these embodiments are intended to allow passage of drug from a reservoir means 134 through a manifold 106 into a drug conduit 108, associated in any of a number of different ways (see FIGS. 2A–3I) with laser delivery means 102. Thereafter, the laser delivery means can be directed through any one of a plurality of laser delivery means handpiece apparatus, including finger tip devices, guide block devices, J-grip handpieces, etc. Such handpieces, with features including but not limited to fiber advance means, depth stop adjust means, rotation control means as well as other auxiliary control mechanisms, are more fully described in co-pending U.S. patent applications Ser. No. 08/675,698 and Ser. No. 08/675,732, both filed Jul.

3, 1996, as well as Ser. No. 08/664,956 filed on Jun. 13, 1996. Additionally, laser delivery may be provided to the target tissue without a handpiece, and may also be directed through a waveguide or articulated arm.

Referring now to FIGS. 4A through 5, laser delivery means adapted for in-line drug delivery apparatus 104 includes an elongated housing 132. The housing 132 contains means for controllably dispensing, in precise amounts as desired, drug contained within the housing 132. As shown, the means for controllably dispensing such substances includes one or more drug reservoirs 134, in this case a type of syringe. A piston or plunger 136 is moved axially by lead arm 138, driven by lead screw 140. A power source 142, such as a battery, powers a small motor 144, coupled to the lead screw 140 by means of gearhead 146. In a preferred embodiment, a stepper motor is capable of providing precise, repeated small drug boluses. The motor is actuated by signals generated and received by controller 148, for example electronics mounted on a printed circuit board. A laser delivery means 102 is also mounted in a fixed, non-movable position within the housing 132, and extends through the housing 132 to a handpiece or other distal tip apparatus (not shown) positioned in operative relationship to the target surface.

In operation, once the drug reservoir is filled, the piston 136 will be positioned in an extended position, as shown. When actuated, the piston 136 will be driven in direction C. Resultant flow of metered quantities of drug will be through the one or more drug ports 128 and into the manifold 106. From there, drug flow is through drug channel 118 surrounding laser delivery means 102, from the proximal end 120 toward the distal end 122 of drug conduit 108.

A preferred embodiment of the in-line drug delivery apparatus 104 can include any of a wide range of types of drug reservoirs 134, and may include more than one reservoir for dispensing several different drugs therefrom. Typical reservoir volumes are 1, 2 and/or 3 milliliters. Typical aliquots, as integral fractions of a complete piston stroke, for dispensing in an automated manner, i.e. upon activation of some button or switch which would at least initiate drug flow and then either continue until released or be otherwise deactivated, or continue for a predetermined time or volume of delivery, are $1/30$, $1/50$, $1/100$ and $1/300$ of the entire reservoir volume. By selecting specific reservoir volume, aliquot fractional amount and control of drug concentration within said drug reservoir, essentially any preselected volume or other amount of drug can be accurately delivered hereby. A selector means such as a selector switch (not shown) is optionally located inside the housing 132 in a portion of the housing for such user settings selection. A clear plastic door covering such selector means provides immediate information to the operator of the apparatus as to current settings and helps prevent undesired and/or unintentional parameter adjustments. A dispense button 150, when manually depressed, will dispense at least one aliquot. It will be understood that the controller and logic thereof may also be programmed to dispense a series of aliquots, at predetermined time intervals or according to other parameters, into the drug channel 118 defined by the drug conduit 108.

Figure 6:
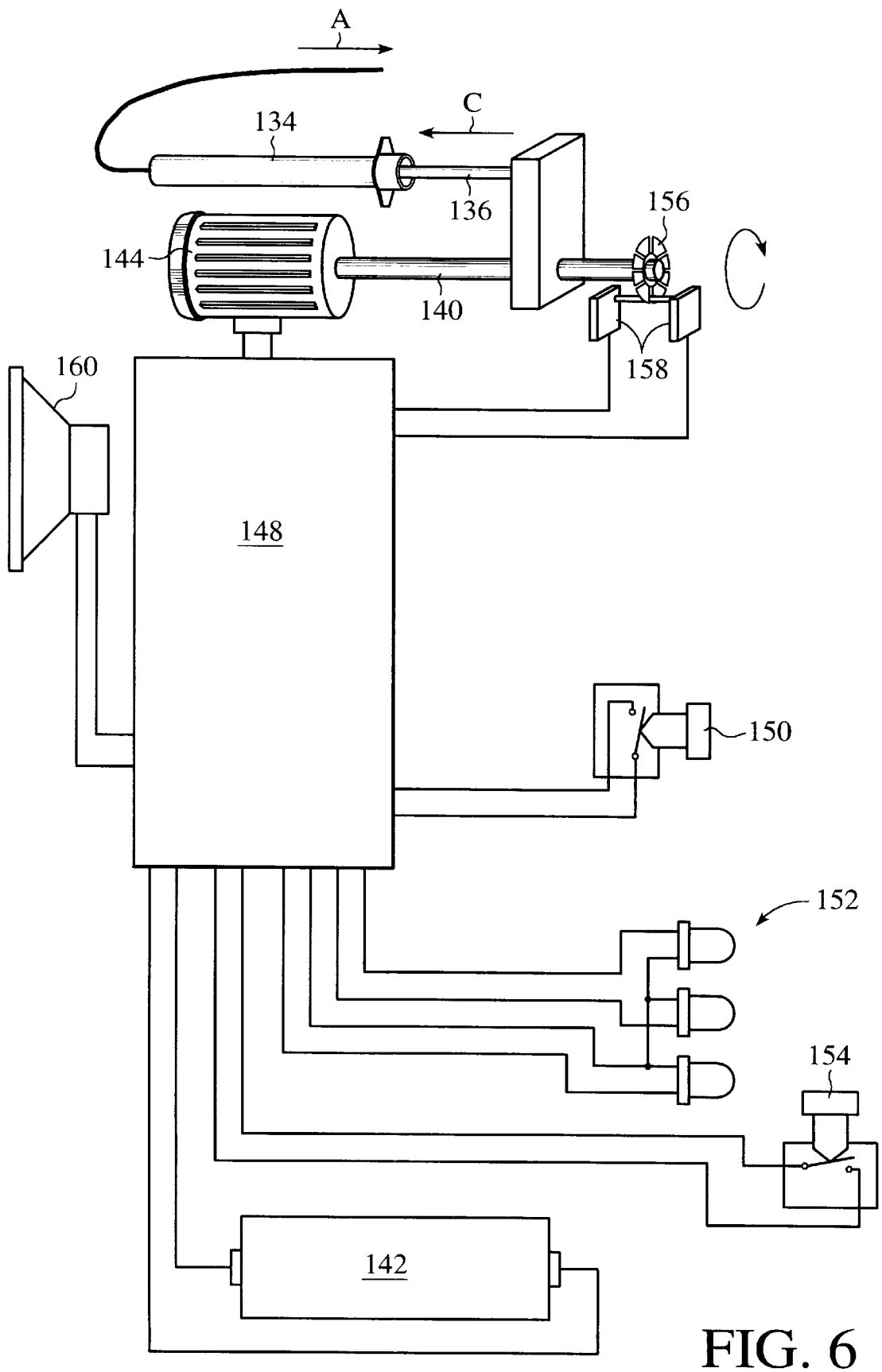
FIG. 6 is a representative electronics block diagram of a preferred embodiment of a laser delivery means adapted for drug delivery apparatus of the present invention.

FIG. 6 is a representative electronics block diagram of a preferred embodiment of a laser delivery means adapted for in-line drug delivery apparatus of the present invention. It will be understood that the following is representative of a single embodiment of the present invention, a large number of additional preferred embodiments will be readily apparent and included within the scope of the present invention. Power source 142 will permit illumination of one of a plurality, more or less, of aliquot size indicator lights 152. Aliquot size selection means 154, typically a toggle or push button type switch, will permit the user to verify and/or select the size of the aliquot to be operatively dispensed.

Based on the foregoing, it will be understood that drug delivery is initiated, in a preferred embodiment of the present invention, by manual activation of dispense activation means 150, such as a toggle or push button, make and break switch, etc. Such dispense activation means 150 will send a signal directly to controller 148 to dispense one or more aliquots in a predetermined time period. Controller 148 will actuate motor 144 so as to cause rotation of lead screw 140. Optical flag 156, configured to rotate in unison with lead screw 140, will allow detection of rotation of lead screw 140 by sensors 158. Such sensors may include infrared LED sensors, motion sensors, etc. As rotation occurs, piston 136 is driven toward drug reservoir 134 in direction C, thus dispensing a predetermined amount of drug in direction A through the one or more drug ports 128, drug conduit 108 and perforations 124. Alternatively, as described above, a small stepper motor will provide individual, sequential delivery of drug aliquots having predetermined volumes. Completion of a dispense cycle, i.e. dispensing of either one or more individual aliquots, will be audibly indicated by cycle complete indicator means 160. Such cycle complete indicator means 160 could comprise a beeper to produce a beep or series of beeps or other audible sounds, or to activate indicator lights, etc. Such cycle complete indicator means 160 could also be configured and/or actuated to indicate an empty drug reservoir, other transient or set operation parameters, apparatus diagnostics, etc.

Figure 7A:
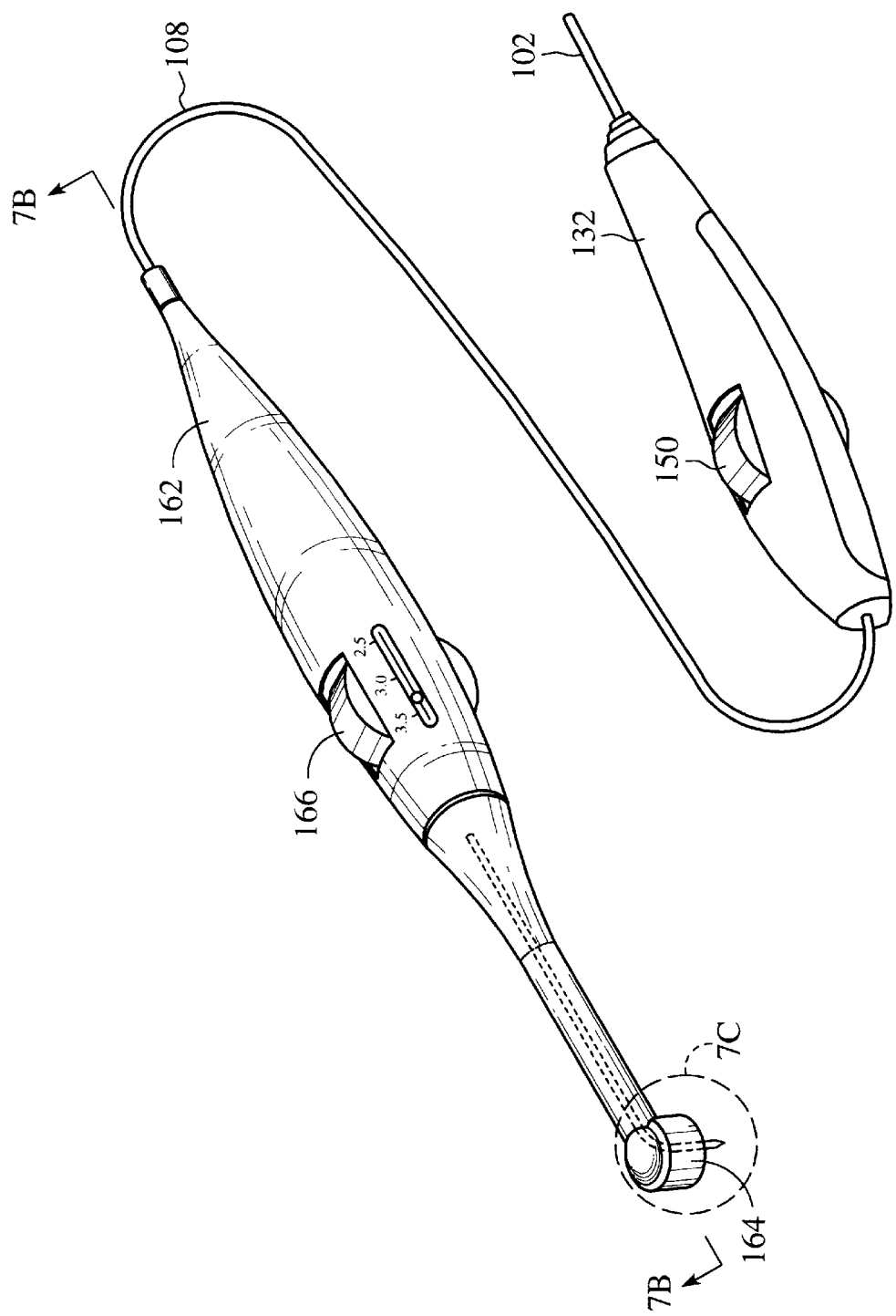
FIG. 7A is a representative perspective view of a preferred embodiment of a hand-held TMR means in conjunction with an in-line laser delivery means of the present invention.
Figure 7B:
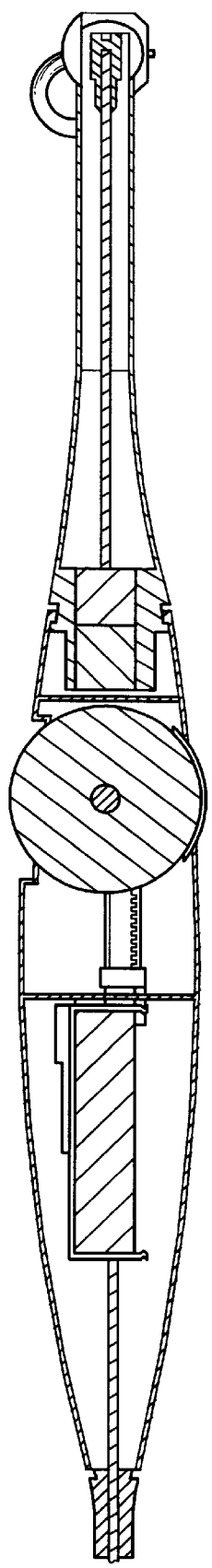
FIG. 7B is a representative cross section view of a preferred embodiment of a hand held laser delivery means adapted for drug delivery apparatus of the present invention.
Figure 7C:
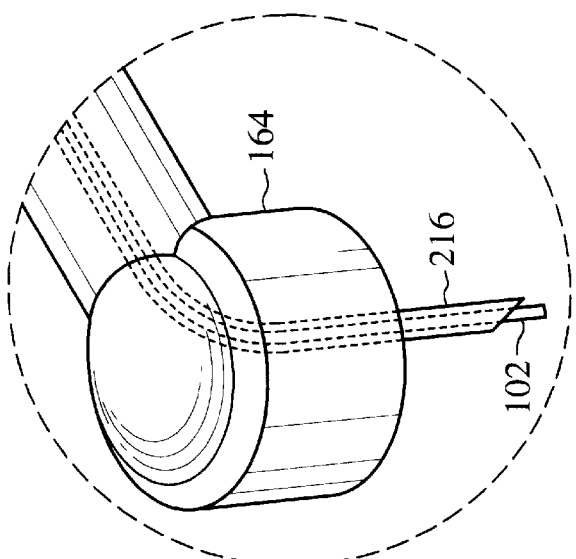
FIG. 7C is a representative detail view of a preferred embodiment of the distal tip of a hand held laser delivery means adapted for drug delivery apparatus of the present invention.

FIG. 7A is a representative perspective view of a preferred embodiment of a laser delivery means adapted for in-line drug delivery apparatus 104 of the present invention in conjunction with a hand held laser handpiece 162. FIG. 7B is a representative cross section view of a preferred embodiment of such a laser handpiece 162. FIG. 7C is a representative detail view of a preferred embodiment of such a laser handpiece 162.

It will be understood that in the field of medical laser technology, in particular with regard to recent advances in the field of TMR, numerous laser handpieces 162 are known. Such laser handpieces 162 will include, and are not limited to, hand-held devices with fiber advance mechanisms, fiber rotating mechanisms, mechanisms for securing a TMR head to a specific point on the heart, such as any of various suction-type devices, or within a chamber of the heart, catheter devices for vascular approaches to the heart, intracoronary TMR devices, preformed or shapeable devices for positioning one or more TMR channels precisely and accurately, etc. Alternatively, fibers may be used without handpieces or laser energy may be delivered through articulating arms with or without waveguides. The laser handpiece 162 shown is hand-held, wand shaped, and has a head portion 164 which is placed against or adjacent myocardium to be revascularized or otherwise treated. A thumbwheel 166 is used to advance the distal end 112 of the laser delivery means 102 within the distal end 122 of the drug conduit 108 containing the drug transmitted therethrough for forming a plurality of laser created openings, such as TMR channels.

In the detail view shown in FIG. 7C, a needle 216 is disposed adjacent head 164 of laser handpiece 162. The hollow needle 216 is used to pierce a surface of the target tissue for creation of a laser-created opening therein. Either prior to, simultaneously with the mechanical piercing, or subsequent thereto, the laser delivery means 102 adapted for in-ine drug delivery of the present invention can be extended through the needle 216. As described above, it will be understood that when employing either a percutaneous approach or a surgical approach, a piercing needle 216 at the distal end 112 of the laser delivery means 102 can be used initially to pierce a surface of the target area. This will minimize bleeding from the epicardium, improve visibility in the region and reduce the incidence of adhesions between the epicardial surface and the pericardial sac. Furthermore, in a catheter assembly used in a vascular approach, such piercing will stabilize the device, for example on the surface of the heart or from within a heart chamber. Then, advancing or retracting a fiber or other laser delivery means a predetermined distance into or out of myocardium while simultaneously delivering laser energy will create an opening, such as a TMR channel or other treatment site, for delivery of drugs, solutions or other substances therein.

Figure 8:
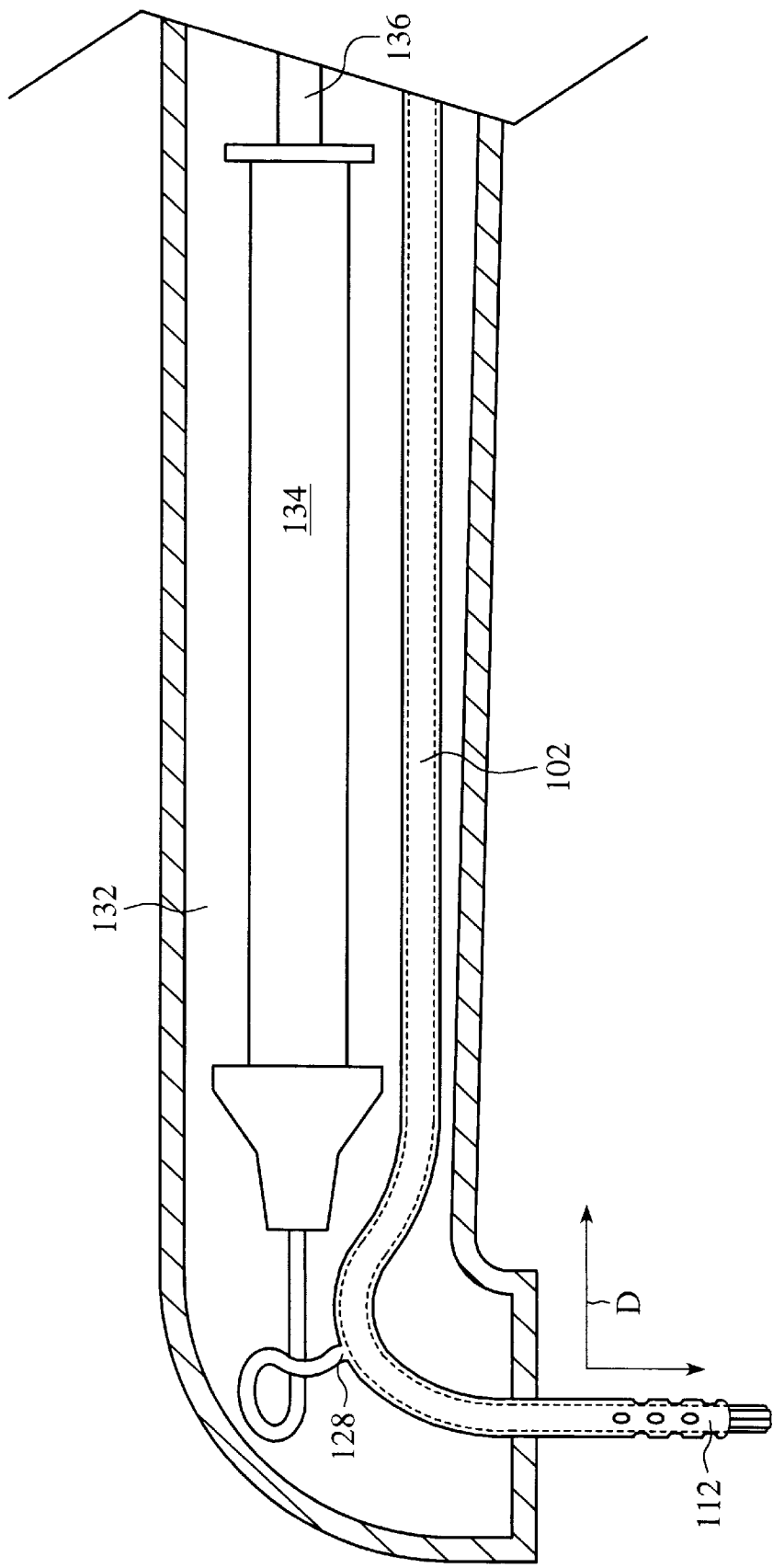
FIG. 8 is a representative partial view of preferred embodiment of a hand held laser delivery means with advance means adapted for drug delivery apparatus of the present invention.

FIG. 8 is a representative partial view of preferred embodiment of a hand held laser delivery means with advance means adapted for drug delivery apparatus of the present invention. As shown, the laser delivery means 102 will be advanced and retracted in directions D, and thus, drug port 128 will also be non-stationary. Therefore, to allow relative movement between the drug port 128 where the drug is supplied to drug channel 118, a section of flexible tubing material 310 is coupled between drug reservoir 134 and the proximal end 120 of drug conduit 108. Drug communication between the reservoir 134 and the drug conduit 108 is therefore maintained, even during advance of the laser delivery means 102.

Figure 9:
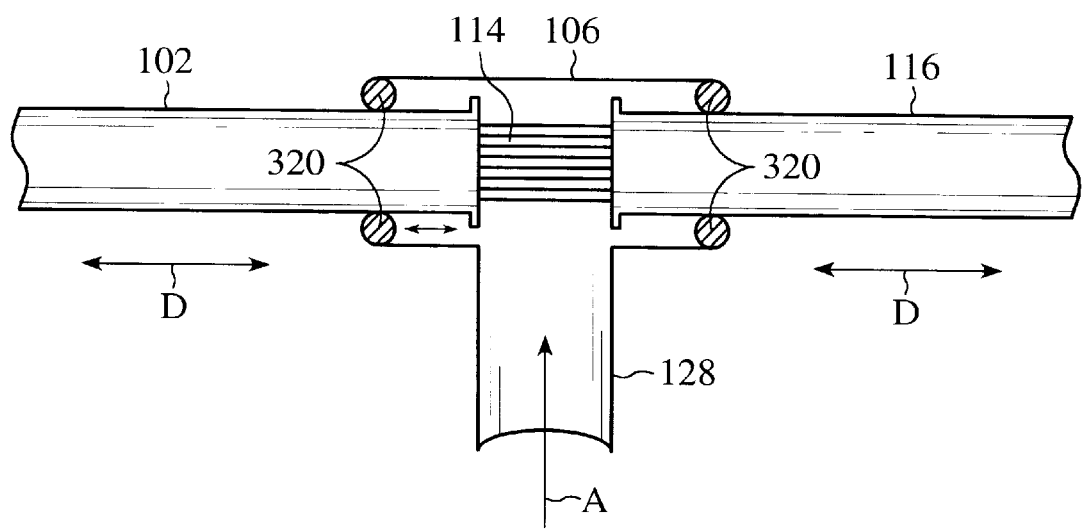
FIG. 9 is a representative partial view of preferred embodiment of a hand held laser delivery means with advance means adapted for drug delivery apparatus of the present invention.

FIG. 9 is a representative partial view of preferred embodiment of a hand held laser delivery means with advance means adapted for drug delivery apparatus of the present invention. In this partial view, it will be understood that a similar type of aperture manifold 106 as shown in FIG. 4B is utilized. Drug flow in direction A will cause drug flow between outer jacket 116 and individual fibers 114 of laser delivery means 102. Thereafter, lateral fiber advancement and retraction in directions D will cause the opening in the outer jacket 106 to move within the manifold 106. However, as long as motion of the laser delivery means 102 is limited to the distance shown, fluid seals 320 will prevent leakage or other loss of drug from the system, for example by flowing the wrong direction through the drug conduit toward the proximal end of laser delivery means 102.

Method of Use

Figure 10:
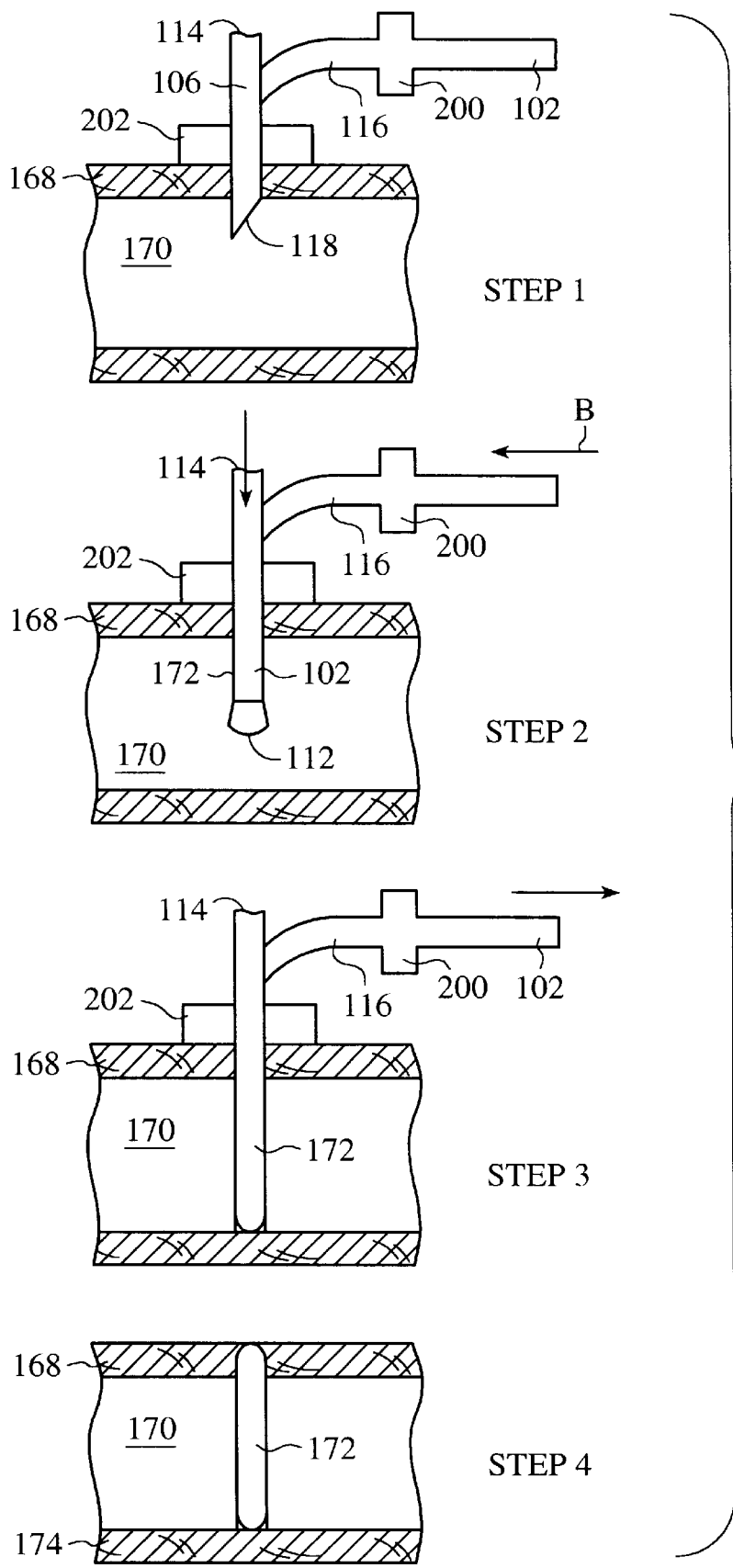
FIG. 10 is a representation of the steps of a method of use of a laser delivery means adapted for drug delivery apparatus of the present invention shown delivering drug to a target area.

FIG. 10 is a representation of the steps of a method of use of a laser delivery means adapted for drug delivery apparatus of the present invention shown delivering drug to a target area. Step 1 shows the distal end 112 of the laser delivery means being inserted through a first surface 168 into target area 170. It will be understood that the first surface 168 can be an epicardial surface, an endocardial surface, or a surface covering or otherwise adjacent tissue of other structures within the human body in which a drug or other substance is to be delivered. It will also be understood that the target surface may be pierced mechanically or by laser energy.

In step 2, a TMR channel or other laser created opening 172 is formed. The TMR channel or other laser created opening 172 can terminate at a point within the target area 170, or can pass entirely through the structure to form an opening through a second surface 174, as shown. The second surface 174 could likewise be either an epicardial surface, an endocardial surface, or other structure defining surface within the human body. At this point, the perforations 124 in the drug conduit 108 will be located at some point within the TMR channel or other laser created opening 172. Alternatively, slight retraction of laser delivery means adapted for in-line delivery of drug will accurately and precisely and operatively position the perforations 124 within the opening 172.

In step 3, drug is dispensed through the perforations 124 of the drug conduit 108 so as to enter the opening 172. In step 4, the drug conduit 108 with laser delivery means 102 is retracted from the opening 172, the dispensed drug remaining therein, or flushing through the channel for TMR type procedures with channels or other laser created openings through the endocardium or other surfaces. The above steps comprise one method of drug delivery. Other steps may include delivery of drug following piercing, or following partial creation of a channel followed by additional lasing.

FIGS. 11A–11E are representative channel diagrams and regions of drug delivery therein possible with a laser delivery means adapted for in-line drug delivery apparatus of the present invention. As described, a single TMR channel or other laser created opening 172 can be formed with the present invention. Such opening can originate from any first surface 168 of essentially any structure within the human body. A wye ("Y") shaped TMR channel or other laser created opening 176 can also be formed. In this case, it is particularly advantageous to deposit drug at or near the branch 178 of the wye ("Y") shaped opening 176. It will be understood that such drug could be deposited at essentially any point within the wye ("Y") shaped opening 176. Similarly, in the case of a vee ("V") shaped TMR channel or other laser created opening 180, drug solution or other substance can be deposited at essentially any point therein. Additionally, drug may be deposited in a blind channel or in some but not all openings or channels.

Figure 11A:
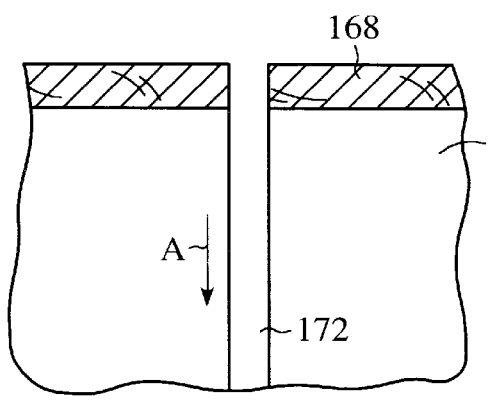
FIGS. 11A–11E are representative channel diagrams and regions of drug delivery therein possible with a laser delivery means adapted for drug delivery apparatus of the present invention.
Figure 11B:
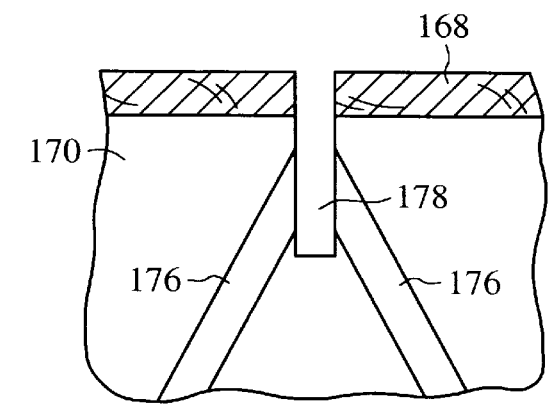
Figure 11C:
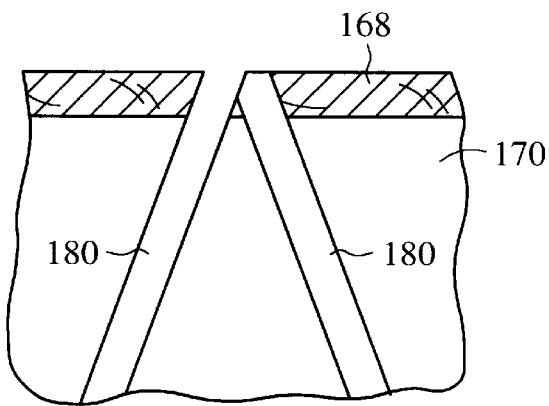
Figure 11D:
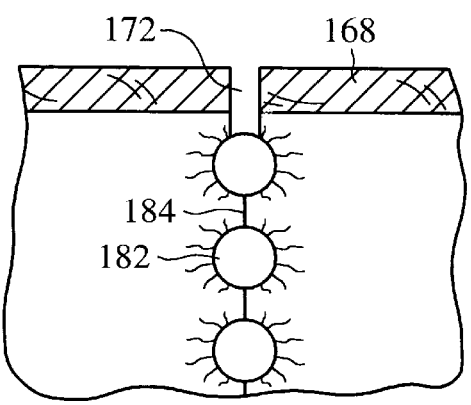
Figure 11E:
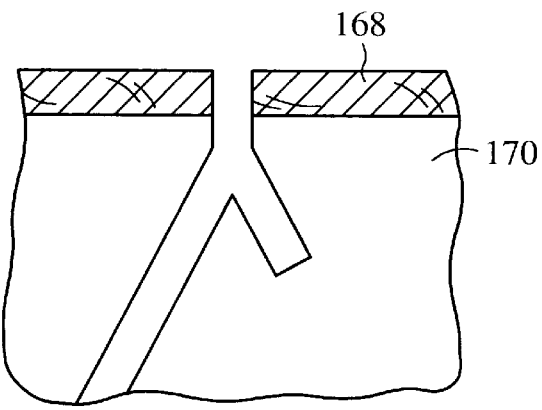

It will be noted that FIG. 11E shows a "blind" or dead-end channel 330. As made clear by the foregoing, these types of channels will be especially suited for drug delivery, especially with regard to drug solids, pellets, time release formulations, etc. Such channel patterns can be created often by making a single opening at the surface, creating a first channel in a first, predetermined angle, retracting the laser delivery means and reorienting the device so as to form one or more subsequent channels at different angles to each other. Additionally, a TMR channel could be created just a short distance below and essentially parallel to the surface of the tissue. Such revascularization just below the typically 1–3 millimeter boundary layer of surface capillaries will encourage their growth downward into muscle, deeper myocardium or other parts of the tissue.

As described above and will be included within the scope of this invention, such laser created openings, including TMR channels, can be open ended or closed at one end. Additional important features of the present invention allow saline or other flushing solution liquids or gases to flush the laser created opening or channel, thereby providing accurate dosing as well as useful cleaning and cooling functions.

It will be understood that while the present invention has been described for performing TMR on heart surfaces, the apparatus and methods described herein are equally intended for use in any suitable procedure in which drug is to be deposited into portions of the body using laser energy to gain access to the depository site. Another procedure known as "stimulation", for example, is performed by using laser energy to create zones or pockets 182, optionally interconnected at least initially by small interconnecting channels 184 ablated through the tissue, for the introduction of blood born growth and healing factors and stimulated capillary growth surrounding the lased zones or pockets to create an increased supply of oxygen to the tissue and thus a revitalization of the heart muscle or other body tissue. Drug can be deposited into the zones or pockets. Methods and apparatus for causing stimulation are more fully described in co-pending U.S. patent application Ser. No. 08/664,956 filed Jun. 13, 1996.

Alternatively, retro-lasing can also be performed using the apparatus and methods of the present invention. This novel use includes the steps of advancing a fiber or other laser delivery means, preferably with a piercing tip, a predetermined distance into the myocardium and then delivering laser energy to create a TMR channel or other treatment site while retracting the fiber, laser delivery means or other functional device. Therefore, with regard to percutaneous TMR, inasmuch as laser energy is only delivered during retraction of the fiber, the possibility of advancing the fiber too far and lasing through the epicardium is eliminated, as are complications arising from such epicardial perforations including but not limited to cardiac tamponade (a buildup in the pericardial sac of an excess of fluid such as blood), proliferation of adhesions, etc. However, with regard to drug delivery, drug can be deposited at essentially any operative time within the procedure, either during piercing, after piercing, during retro-lasing or at some point thereafter.

Adjunct use of appropriate blood seal means, depth stop apparatus such as clamps, etc., visualization means, marker means as well as other hardware and methodology will be considered within the scope of the present invention. Visualization can be enhanced with ultrasound or by using radio-opaque materials for construction, metal or other material foils or bands, especially at or adjacent distal ends of the optical fibers or as part of the drug solution formulations themselves. This will assist the practitioner in fluoroscopy or other visualization methodology for precise and accurate positioning of the apparatus and deposit of drug solutions and other substances. Additionally, visualization will also be useful to the physician for observing the drug delivery process and/or the drug activity within the channel or pocket.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers with and without piercing tips and with or without firing tips or fiber ends having shaped or contoured end faces for selectively diverging the laser beam or other laser energy diverging means, cable, rods, articulated arms, mirror configurations and other laser delivery means with and without focusing lens and the like. It will also be understood that the apparatus and method of the present invention as described herein, including the novel combination or use with of any conventional mechanism or method which are known to those skilled in the art, are included within the scope of this invention.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A laser energy delivery system for providing laser and drug treatment to tissue comprising:
    a fiber optic bundle having proximal and distal ends, the proximal end adapted for attachment to a source of laser energy, the distal end delivering laser energy to treat target tissue the fiber optic bundle having at least one drug conduit, the at least one drug conduit having a proximal end and a distal end with at least one drug port; and
    a drug inlet assembly having a passage communicating with the at least one drug conduit, the drug inlet assembly adapted for connection to a source of drug, whereby the laser energy delivery system is extendable into the target tissue to provide laser treatment and to deliver drugs.

2. The laser energy delivery system of claim 1 wherein the optical fiber bundle is surrounded by a jacket.

3. The laser energy delivery system of claim 1 wherein the at least one drug conduit is within the optical fiber bundle and is at least one tubular member having at least one infusion channel.

4. The laser energy delivery system of claim 1 wherein the at least one drug conduit is at least one space between fibers of the fiber optic bundle, the at least one space communicating with the drug inlet and the at least one drug port.

5. The laser energy delivery system of claim 1 wherein the at least one drug port is a permeable membrane surrounding at least the distal end of the fiber optic bundle.

6. The laser energy delivery system of claim 1 wherein the at least one drug conduit further comprises at least one infusion channel extending from the drug inlet assembly to the at least one drug port.

7. The laser energy delivery system of claim 6 wherein at least the distal end of the fiber optic bundle is surrounded by the at least one drug conduit and the at least one infusion channel comprises an annular space between the at least one drug conduit and the fiber optic bundle.

8. The laser energy delivery system of claim 6 comprising first and second drug conduits and first and second infusion channels, the first infusion channel an annular space between the first drug conduit which surrounds the fiber optic bundle and the second infusion channel comprising an interior space of a tubular member within the fiber optic bundle, the system further comprising first and second drug ports, the first drug port at least one perforation through the first drug conduit and the second drug port an open distal end of the tubular member.

9. The laser energy delivery system of claim 1 further comprising at least one seal disposed between the fiber optic bundle and the at least one drug conduit proximal the drug inlet assembly.

10. The laser energy delivery system of claim 9 further comprising a piercing device for mechanically piercing a surface of the target tissue.

11. The laser energy delivery system of claim 9 wherein the piercing device is a tapered distal tip of the fiber optic bundle.

12. The laser energy delivery system of claim 9 wherein the piercing device is a tapered distal tip of the drug conduit.

13. The laser energy delivery system of claim 1 further comprising at least one drug reservoir connected to the drug inlet assembly.

14. The laser energy delivery system of claim 13 further comprising one or more dispensers operatively connected to the at least one drug reservoir.

15. The laser energy delivery system of claim 1 further comprising a housing adapted for mounting the source of drug therein, the housing further defining an actuator for dispensing drug from the source of drug into the drug inlet assembly and a selector for setting an amount of drug for delivery.

16. The laser delivery system of claim 15 wherein the distal portion of the optical fiber bundle extends through the housing and the distal end of the at least one drug inlet assembly communicates with the drug conduit within the housing.

17. The laser delivery system of claim 15 further comprising an optical fiber bundle housing and the distal end of the drug inlet assembly is one or more tubes extend from the housing to the optical fiber bundle housing.

18. The laser energy delivery system of claim 15 further comprising a power source mounted in the housing and operatively connected to the actuator for automatic drug dispensing.

19. A method for providing laser treatment and drug delivery to a human body site comprising the acts of:

providing an assembly including a fiber optic bundle having at least one drug conduit, the assembly having proximal and distal ends, the proximal end adapted for attachment to a source of laser energy, the assembly further comprising a drug inlet adapted for connection to a source of drug and connected to the at least one drug conduit, the at least one drug conduit having at least one drug port at a distal end thereof;

positioning a distal end of the fiber optic bundle adjacent the human body site;

delivering laser energy from the distal end of the fiber optic bundle to treat the site;

and dispensing a selected drug through the at least one drug port to the site.

20. The method of claim 19 further comprising the additional act of:

re-positioning the distal end of the fiber optic bundle adjacent additional human body sites.

21. The method of claim 19 in which the distal end of the fiber optic bundle further comprises a piercing device and the method further comprises the act of:

mechanically piercing a surface of the site prior to delivering laser energy to the site.

22. The method of claim 19 further comprising providing a drug dispenser and at least one reservoir containing one or more drugs for attachment to the drug inlet, the method further comprising the act of: activating the drug dispenser to dispense the one or more drug to the site.

23. The method of claim 22 in which the drug dispenser is a manually activated plunger.

24. The method of claim 22 in which the drug dispenser is a switch operatively connected to a power source.

25. The method of claim 19 wherein the act of dispensing occurs simultaneously with the act of delivering laser energy.

26. The method claim 19 wherein the act of delivering laser energy includes the act of removing tissue.

27. The method of claim 19 wherein the act of positioning includes placing the fiber optic bundle adjacent a wall of the heart, the act of delivering laser energy includes forming at least one myocardial revascularization channel within myocardial tissue, and the act of dispensing selected drugs includes dispensing an angiogenic agent into the channel.

28. The method of claim 27 further comprising the act of piercing the wall of the heart prior to delivering laser energy.

29. The method of claim 27 wherein the forming the at least one myocardial revascularization channel includes the act of advancing the fiber optic bundle into the myocardial tissue.

30. A catheter for providing laser and drug treatment to tissue comprising:

a longitudinally extending tube having at least a first lumen;

a fiber optic bundle having proximal and distal ends mounted within the first lumen, the proximal end adapted for attachment to a source of laser energy, the distal end delivering laser energy to treat target tissue, the fiber optic bundle having at least one drug conduit having a proximal end and a distal end with at least one drug port; and at least one drug inlet assembly having a passage communicating with the at least one drug conduit, the at least one drug inlet assembly adapted for connection to one or more sources of drug, whereby the fiber optic bundle and at least one drug conduit are extendable into the target tissue to provide laser treatment and to deliver drugs from the first lumen.

31. The catheter of claim 30 wherein the at least one drug conduit is at least one tubular member within the fiber optic bundle.

32. The catheter of claim 30 wherein the at least one drug conduit is at least one annular space between fibers of the fiber optic bundle.

33. The catheter of claim 30 wherein the at least one drug port is a semipermeable membrane.

34. The catheter of claim 30 further comprising a seal surrounding the fiber optic bundle and positioned proximal to the drug inlet assembly.

35. The catheter of claim 30 further comprising a piercing device for mechanically piercing a surface of the target tissue.

36. The catheter of claim 30 further comprising one or more dispensers operatively connected to the at least one drug reservoir.

37. The catheter of claim 30 further comprising a housing connected to a proximal end of the longitudinally extending tube and having the source of drug mounted therein, the housing further defining an actuator for dispensing drug from the source of drug into the drug inlet assembly and a selector for setting an amount of drug for delivery.

38. The catheter of claim 37 further comprising a power source mounted in the housing and operatively connected to the actuator for automatic drug dispensing.

* * * * *